(12) United States Patent
Yamamoto

(10) Patent No.: US 10,786,228 B2
(45) Date of Patent: Sep. 29, 2020

(54) ULTRASOUND DIAGNOSTIC APPARATUS, SOUND VELOCITY DETERMINING METHOD, AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 699 days.

(21) Appl. No.: 14/669,646

(22) Filed: Mar. 26, 2015

(65) Prior Publication Data

US 2015/0196283 A1    Jul. 16, 2015

Related U.S. Application Data

(63) Continuation of application No. PCT/JP2013/075485, filed on Sep. 20, 2013.

(30) Foreign Application Priority Data

Sep. 27, 2012  (JP) .................................. 2012-215258
Jul. 11, 2013   (JP) .................................. 2013-145442

(51) Int. Cl.
*A61B 8/08*    (2006.01)
*A61B 8/00*    (2006.01)
(Continued)

(52) U.S. Cl.
CPC .......... *A61B 8/5269* (2013.01); *A61B 8/0825* (2013.01); *A61B 8/4245* (2013.01);
(Continued)

(58) Field of Classification Search
CPC ... A61B 8/5261; A61B 8/4245; A61B 8/0825; A61B 8/485; A61B 8/4416; A61B 8/58;
(Continued)

(56) References Cited

U.S. PATENT DOCUMENTS

| | | | | |
|---|---|---|---|---|
| 5,570,691 A | * | 11/1996 | Wright | ................ G01S 7/52049 600/447 |
| 2001/0014773 A1 | * | 8/2001 | Jago | .................... G01S 7/52036 600/437 |

(Continued)

FOREIGN PATENT DOCUMENTS

| | | | |
|---|---|---|---|
| JP | 9-224938 A | 9/1997 | |
| JP | 1997224938 A | * 9/1997 | ............... A61B 8/00 |

(Continued)

OTHER PUBLICATIONS

Hemmsen et al. 2012 Ultrasound Med. Biol. 38:708-716 (Year: 2012).*

(Continued)

*Primary Examiner* — Jeffrey G Hoekstra
*Assistant Examiner* — Patrick M Mehl
(74) *Attorney, Agent, or Firm* — Birch, Stewart, Kolasch & Birch, LLP

(57) ABSTRACT

In the ultrasound diagnostic apparatus, the method of determining the sound velocity, and the program recorded in a recording medium, a probe is made transmit an ultrasonic beam a plurality of times so as to form a predetermined transmission focus point, an analog element signal output by the probe is A/D converted into the first element data, the second element data corresponding to any one of a plurality of the first element data is generated, and the second element data is used to determine the sound velocity in an inspection object, whereby the sound velocity of the ultrasonic waves in the inspection object can be accurately determined without decreasing the frame rate.

21 Claims, 10 Drawing Sheets

(51) Int. Cl.
*G01S 15/89* (2006.01)
*G10K 11/34* (2006.01)
*G01S 7/52* (2006.01)
*A61B 8/14* (2006.01)

(52) U.S. Cl.
CPC .......... *A61B 8/4416* (2013.01); *A61B 8/4488* (2013.01); *A61B 8/485* (2013.01); *A61B 8/5261* (2013.01); *A61B 8/58* (2013.01); *G01S 7/52049* (2013.01); *G01S 15/8915* (2013.01); *G10K 11/346* (2013.01); *A61B 8/14* (2013.01); *A61B 8/5207* (2013.01)

(58) Field of Classification Search
CPC ............. G01S 15/8915; G01S 7/52049; G01S 7/52095; G10K 11/346; G10K 2210/3215; G10K 2021/02166; G10K 2200/10
See application file for complete search history.

(56) References Cited

U.S. PATENT DOCUMENTS

| | | | |
|---|---|---|---|
| 2009/0099456 A1* | 4/2009 | Burcher | A61B 8/00 600/459 |
| 2010/0036251 A1* | 2/2010 | Baba | G10K 11/346 600/447 |
| 2011/0077518 A1* | 3/2011 | Miyachi | A61B 5/02007 600/443 |
| 2011/0077519 A1 | 3/2011 | Katsuyama | |
| 2013/0267849 A1 | 10/2013 | Katsuyama | |
| 2013/0296706 A1 | 11/2013 | Katsuyama | |
| 2013/0303912 A1 | 11/2013 | Katsuyama | |

FOREIGN PATENT DOCUMENTS

| | | | | |
|---|---|---|---|---|
| JP | 2004-522515 A | | 7/2004 | |
| JP | 2009-78124 A | | 4/2009 | |
| JP | 2009078124 A | * | 4/2009 | ............... A61B 8/00 |
| JP | 2011-92686 A | | 5/2011 | |
| WO | WO 2012/043569 A1 | | 4/2012 | |

OTHER PUBLICATIONS

International Preliminary Report on Patentability and English translation of the Written Opinion of the International Searching Authority (Forms PCT/IB/338, PCT/IB/373 and PCT/ISA/237), dated Apr. 9, 2015, for International Application No. PCT/JP2013/075485.
Japanese Notification of Reasons for Refusal for Japanese Application No. 2013-145442, dated Jun. 7, 2016, with Machine Translation.
Japanese Office Action, dated Oct. 27, 2015, for Japanese Application No. 2013-145442, with a partial English translation.
International Search Report, issued in PCT/JP2013/075485, dated Dec. 10, 2013.

* cited by examiner

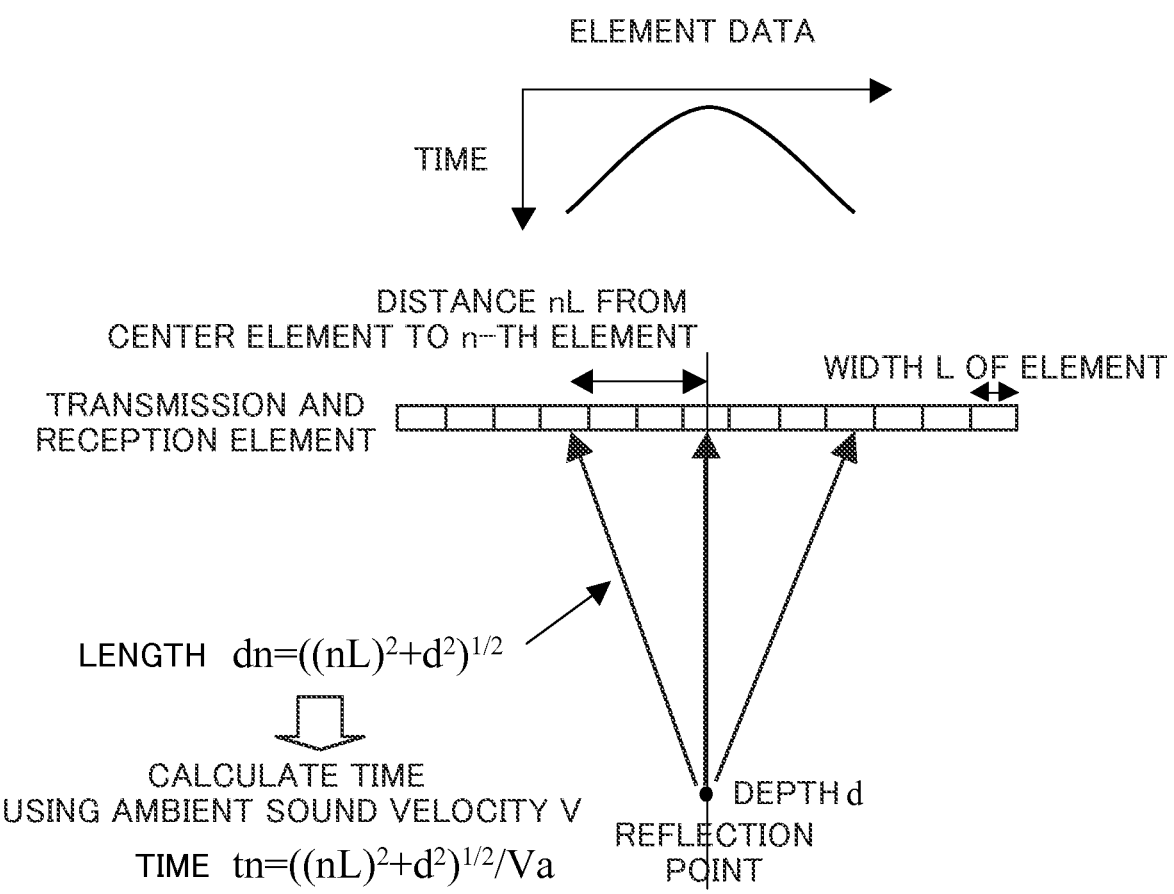

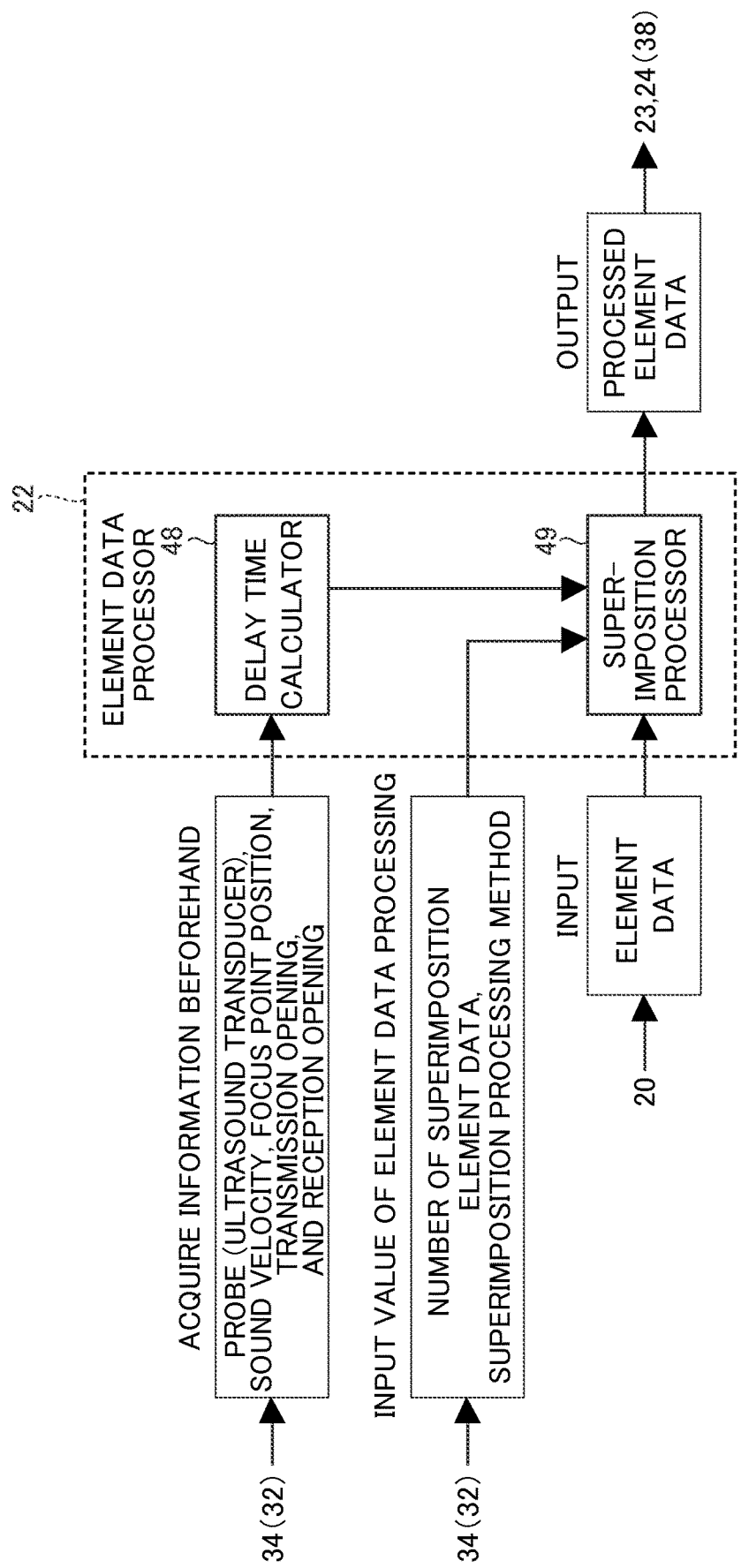

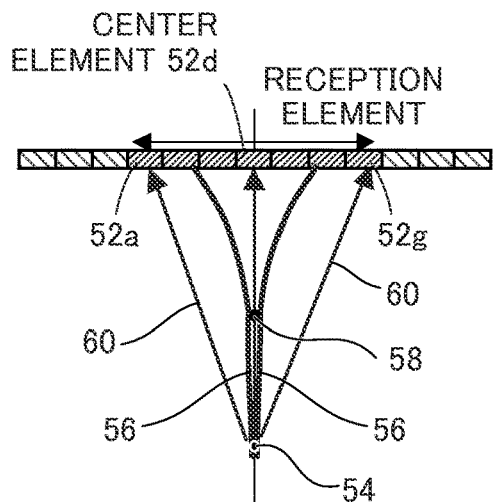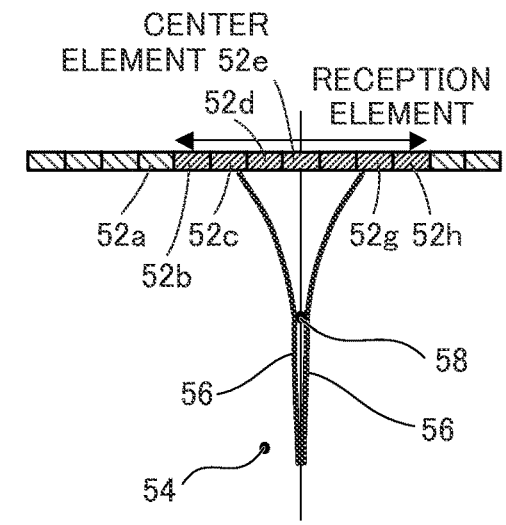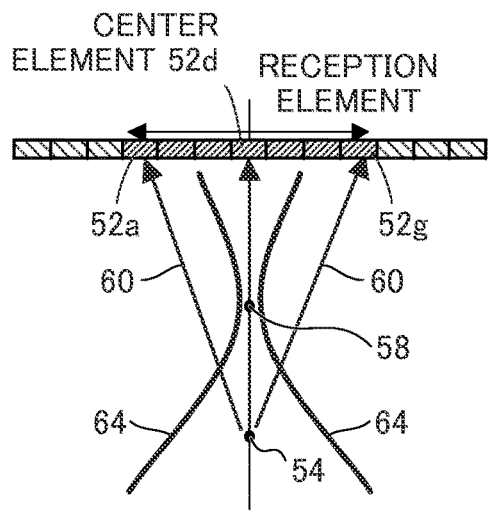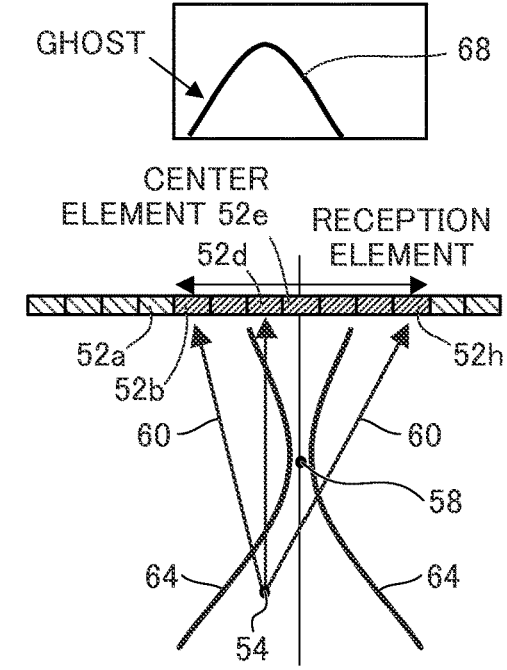

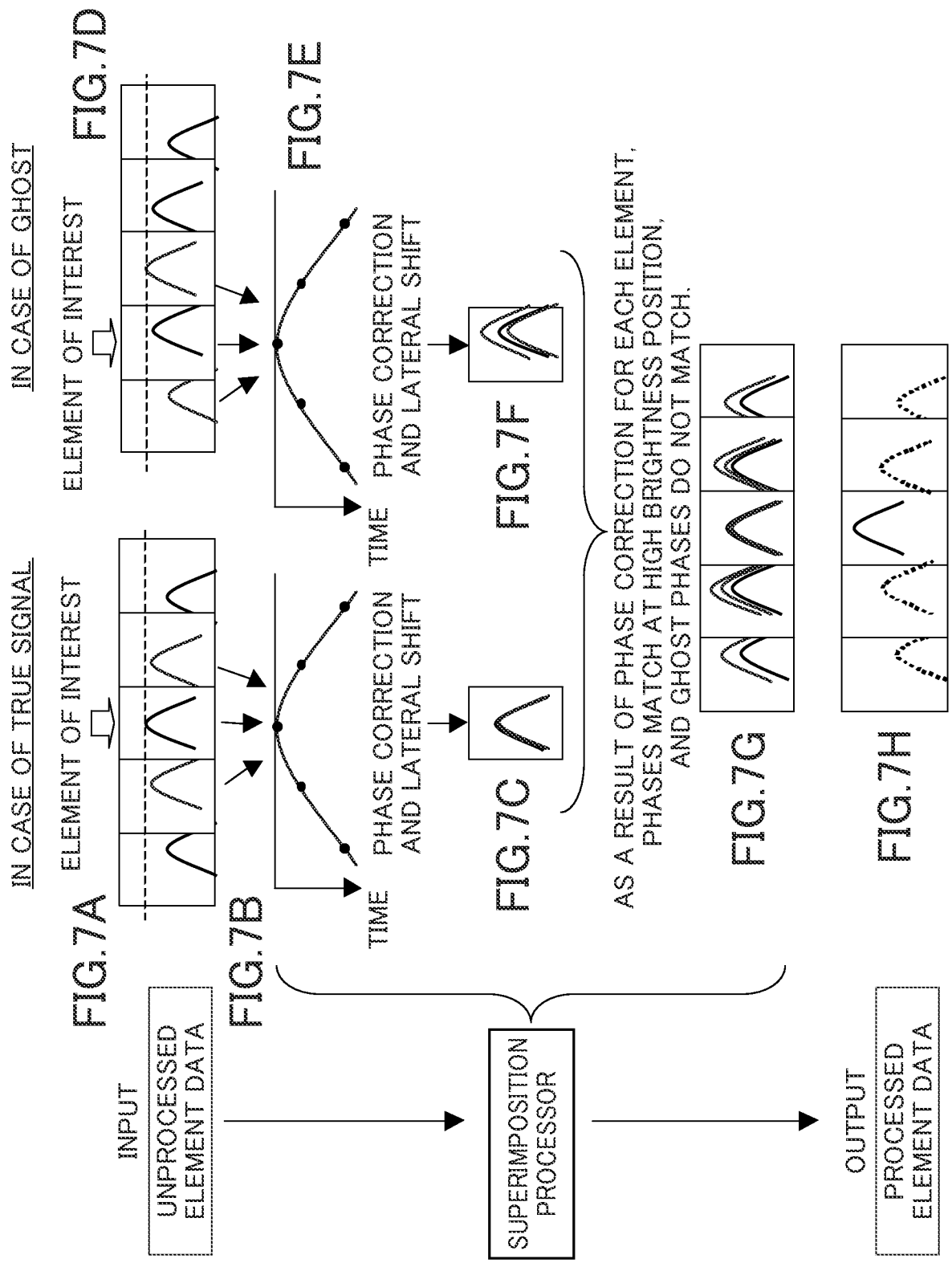

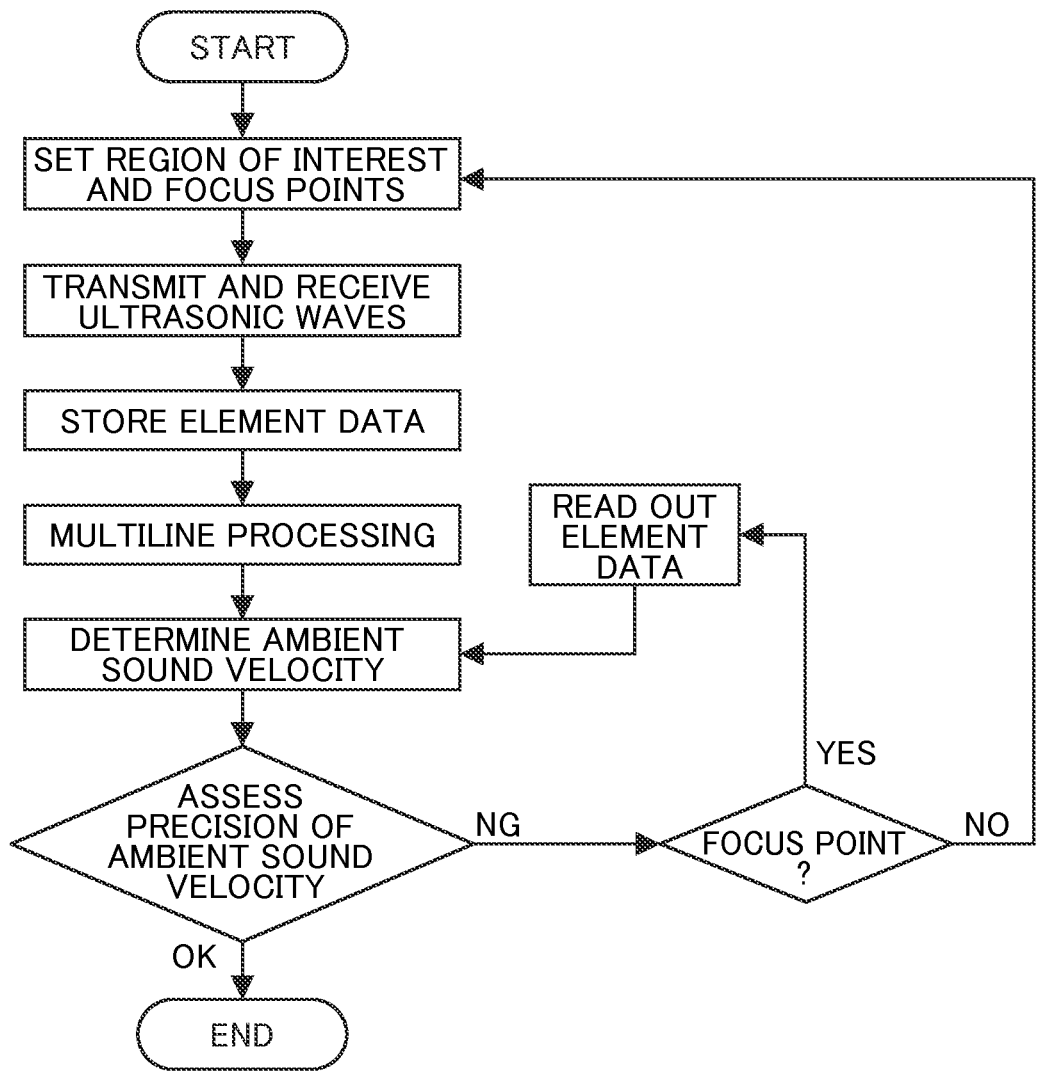

ULTRASOUND DIAGNOSTIC APPARATUS, SOUND VELOCITY DETERMINING METHOD, AND RECORDING MEDIUM

CROSS-REFERENCE TO RELATED APPLICATIONS

This application is a Continuation of PCT International Application No. PCT/JP2013/075485 filed on Sep. 20, 2013, which claims priority under 35 U.S.C. § 119(a) to Japanese Application No. 2012-215258 filed on Sep. 27, 2012 and Japanese Application No. 2013-145442 filed on Jul. 11, 2013. Each of the above application(s) is hereby expressly incorporated by reference, in its entirety, into the present application.

BACKGROUND OF THE INVENTION

The invention relates to, in an ultrasound diagnosis, an ultrasound diagnostic apparatus having a function of determining a sound velocity inside an inspection object, a method of determining a sound velocity inside an inspection object, and a recording medium a program determining a sound velocity of an inspection object is recorded.

Conventionally, ultrasound diagnostic apparatuses such as ultrasound image diagnostic apparatuses using ultrasound images are put to practical use in the medical field.

Generally, this type of ultrasound diagnostic apparatus has an ultrasound probe (hereinafter, referred to as "probe") with a plurality of built-in elements (ultrasound transducers) and an apparatus main body connected with the probe. In the ultrasound diagnostic apparatus, an ultrasonic beam is transmitted toward a subject (an inspection object) so as to form a predetermined focus point (transmission focus) from the plurality of elements of the probe, an ultrasonic echo from the subject is received in the probe, and an ultrasound image is generated by electrically processing the reception signal of the received ultrasonic echo in the apparatus main body.

Here, in the ultrasound diagnostic apparatus, an ultrasonic echo from a subject according to the transmission of a single ultrasonic beam is received by a plurality of elements. Accordingly, even with ultrasonic echoes reflected by the same reflector, the reception time of the ultrasonic echoes is delayed according to the position of each of the elements.

Therefore, in the ultrasound diagnostic apparatus, an ultrasound image is generated using reception data generated by analog-to-digital (A/D) converting of the reception signal of the ultrasonic echoes received in each of the elements into a digital reception signal (hereinafter, referred to as element data), carrying out a reception focusing process, that is, delay correction on the element data according to a delay time of the reception signal, and performing phase matching and phasing addition.

In conventional ultrasound diagnostic apparatuses, the sound velocity of ultrasonic waves in the subject is assumed to be constant, and the reception focusing process was performed by fixing a sound velocity of the ultrasonic waves to a predetermined certain value.

However, the sound velocity varies depending on the type of tissues such as fatty layers, muscular layers in a living body, and therefore the sound velocity of ultrasonic waves is not uniform in the subject. In addition, the thicknesses of fatty layers and muscular layers are different in overweight subjects and slim subjects. In other words, the sound velocity of ultrasonic waves varies from person to person.

Accordingly, in a conventional ultrasound diagnostic apparatus in which the sound velocity of ultrasonic waves is fixed, when the actual sound velocity in a subject differs from a set sound velocity, the arrival time for the ultrasonic echoes to be reflected inside the subject and reach the elements does not match with a set delay time.

As a result, there is a problem in that proper phase matching is not possible, reception focusing is not properly performed, and the image quality of the obtained ultrasound image deteriorates. In addition, there is also a problem in that the obtained ultrasound image is distorted with respect to the actual subject.

With respect to such problems, in the ultrasound diagnostic apparatus, the sound velocity in the subject is determined (calculated), and the reception focusing process is performed using this sound velocity.

For example, JP 2011-92686 A describes an ultrasound diagnostic apparatus which transmits and receives ultrasonic waves after setting a region of interest where a diagnosis region in a subject is divided in an ultrasound image to be photographed, calculates a focus index for each of a plurality of sound velocities (set sound velocities) set in advance in each region of interest by performing a reception focusing process with respect to obtained element data using a plurality of sound velocities (set sound velocities) set as appropriate, and uses the calculated focus indexes to determine the sound velocity (the ambient sound velocity) in each region of interest.

Examples of the focus indexes include contrast, brightness, and the like. For example, a set sound velocity where the brightness set as the focus index was the highest may be determined as the sound velocity in the region of interest.

SUMMARY OF THE INVENTION

In the ultrasound diagnostic apparatus described in JP 2011-92686 A, an ultrasound image is generated by performing a reception focusing process by correcting or selecting a delay time or delay pattern according to the determined sound velocity. Due to this, regardless of the differences in the sound velocities depending on the location in the subject or among the subjects, it is possible to stably output a proper ultrasound image.

Here, with the method of determining the sound velocity, is possible to determine an accurate sound velocity in a location where a wavefront shape of ultrasonic echoes (reflected waves) is clear. However, it is often not possible to determine an accurate sound velocity at positions separated from a focus point, or the like.

Therefore, depending on the position in the subject (the ultrasound image), there are cases where it is not possible to perform a proper reception focusing process even when using the determined sound velocity and an ultrasound image with a high image quality cannot be obtained.

On the other hand, in order to determine an accurate sound velocity corresponding to every location in the subject, the ultrasound transmission (transmission and reception) may be performed corresponding to a large number of focus points where the positions in the depth and azimuth direction are different.

However, when the ultrasound transmission and reception is performed corresponding to a large number of focus points, there is another problem in that the frame rate of the ultrasound image decreases in accordance with the updating or the like of the sound velocities.

An object of the invention is to solve the problems of the related art techniques and to provide an ultrasound diagnostic apparatus, a sound velocity determining method, and a recording medium recording a program which are able to accurately determine a sound velocity in all locations in an inspection object in an ultrasound diagnosis even without performing transmission and reception of ultrasonic waves corresponding to a large number of focus points in the depth direction.

In order to attain the object described above, the invention provides an ultrasound diagnostic apparatus, which inspects an inspection object using an ultrasonic beam, comprising:

a probe in which a plurality of elements are arranged, which transmit the ultrasonic beam, receive ultrasonic echoes reflected by the inspection object, and output an analog element signal according to the received ultrasonic echoes;

a transmitter configured to make the probe perform transmission of the ultrasonic beam a plurality of times so as to each form a predetermined transmission focus point using the plurality of elements;

a receiver configured to receive an analog element signal output by the plurality of elements corresponding to the individual transmission of the ultrasonic beam, and carry out a predetermined process;

an analog-to-digital (A/D) converter configured to analog-to-digital convert the analog element signal processed by the receiver into first element data which is a digital element signal;

a data processor configured to generate second element data corresponding to any one of a plurality of the first element data; and a sound velocity determiner configured to determine a sound velocity in the inspection object using the second element data.

Preferably, the transmitter makes the probe perform transmission of the ultrasonic beam a plurality of times, changing at least one of a center element and a transmission direction of the ultrasonic beam.

Preferably, the data processor generates the second element data using at least one of a plurality of the first element data obtained by transmission of the ultrasonic beam where the center element is different to each other and a plurality of the first element data obtained by transmission of the ultrasonic beam where the transmission direction is different to each other.

Preferably, the data processor generates the second element data from a plurality of the first element data obtained by transmission of the ultrasonic beam where transmission regions overlap.

Preferably, the data processor generates the second element data by superimposing a plurality of the first element data according to a reception time at which the elements received the ultrasonic echoes and positions of the elements.

Preferably, the ultrasound diagnostic apparatus further comprises an assessment section configured to assess precision of the determined sound velocity.

Preferably, when the precision of the sound velocity is less than a predetermined precision, the transmission focus point is changed and the transmission of the ultrasonic beam is performed again with respect to a position where the sound velocity is less than the predetermined precision and the sound velocity of this position is redetermined.

Preferably, the precision of the redetermined sound velocity is assessed and the redetermining and assessment of the sound velocity are repeated until the precision of the sound velocity is the predetermined precision or more.

Preferably, he ultrasound diagnostic apparatus further comprises: a storage configured to store the first element data; and a position determiner configured to determine whether or not a position inside the inspection object is in a vicinity of a position of the transmission focus point, wherein the first element data corresponding to determination of the sound velocity is stored in the storage, the position determiner determines whether or not the position at which the sound velocity is determined is in a vicinity of the transmission focus point when the precision of the sound velocity is less than the predetermined precision, redetermination of the sound velocity is performed using the first element data without performing transmission of the ultrasonic beam when in the vicinity of the transmission focus point, and the transmission focus point is changed and the transmission of the ultrasonic beam is performed again corresponding to a position where the precision of the sound velocity is less than the predetermined precision and the sound velocity of this position is redetermined when not in the vicinity of the transmission focus point.

Preferably, when the precision of the redetermined sound velocity is less than the predetermined precision, the transmission focus point is changed and the transmission of the ultrasonic beam is performed again with respect to a position where the precision of the sound velocity is less than the predetermined precision, and the sound velocity of this position is redetermined, and the assessment of the precision of the sound velocity is repeated again until the precision of the sound velocity is the predetermined precision or more.

Preferably, the sound velocity is determined in a plurality of positions inside the inspection object and the precision of the sound velocity is assessed at each position.

Preferably, the assessment of the precision of the sound velocity is performed using at least one of variation in the sound velocity, standard deviation in the sound velocity, a difference between a maximum value and a minimum value of the sound velocity, and an average value of the sound velocity.

Preferably, the ultrasound diagnostic apparatus further comprises an element data storage configured to store all of the first element data corresponding to at least one ultrasound image.

Preferably, an ultrasound image is formed using the second element data.

Preferably, an ultrasound image is formed by performing phasing addition for forming the ultrasound image using the sound velocity determined by the sound velocity determiner.

The invention provides a sound velocity determining method for ultrasound diagnosis using a probe in which a plurality of elements are arranged, which transmit an ultrasonic beam, receive ultrasonic echoes reflected by an inspection object, and output an analog element signal according to the received ultrasonic echoes, the method comprising the steps of:

making the probe perform transmission of the ultrasonic beam a plurality of times so as to each form a predetermined transmission focus point using the plurality of elements when determining a sound velocity inside the inspection object and outputting an analog element signal from the plurality of elements corresponding to the individual transmission of ultrasonic beams;

analog-to-digital converting the analog element signal into first element data which is a digital element signal;

generating second element data corresponding to any one of a plurality of the first element data; and determining the sound velocity inside the inspection object using the second element data.

Preferably, the probe is made perform transmission of the ultrasonic beam a plurality of times, changing at least one of a center element and a transmission direction of the ultrasonic beam.

Preferably, the second element data is generated using at least one of a plurality of the first element data obtained by transmission of the ultrasonic beam where the center element is different to each other and a plurality of the first element data obtained by transmission of the ultrasonic beams where the transmission direction is different to each other.

Preferably, the second element data is generated from a plurality of the first element data obtained by transmission of the ultrasonic beam where transmission regions overlap.

Preferably, the second element data is generated by superimposing a plurality of the first element data according to a reception time at which the elements received the ultrasonic echoes and positions of the elements.

Preferably, the sound velocity determining method further comprises assessing precision of the determined sound velocity.

Preferably, when the precision of the sound velocity is less than a predetermined precision, the transmission focus point is changed and the transmission of the ultrasonic beam is performed again with respect to a position where the precision of the sound velocity is less than the predetermined precision, and the sound velocity of the position is redetermined.

Preferably, the precision of the redetermined sound velocity is assessed and the redetermining and assessment of the sound velocity are repeated until the precision of the sound velocity is the predetermined precision or more.

Preferably, the first element data corresponding to the determining of the sound velocity is stored in advance, a position at which the sound velocity is determined is determined to be in a vicinity of the transmission focus point or not when the precision of the sound velocity is less than a predetermined precision, redetermination of the sound velocity is performed using the first element data without performing transmission of the ultrasonic beam when in the vicinity of the transmission focus point, and the transmission focus point is changed and the transmission of the ultrasonic beam is performed again corresponding to a position where the precision of the sound velocity is less than the predetermined precision and the sound velocity of this position is redetermined when not in the vicinity of the transmission focus point.

Preferably, the precision of the redetermined sound velocity is assessed, the transmission focus point is changed and the transmission of the ultrasonic beam is performed again with respect to a position where the precision of the sound velocity is less than the predetermined precision when the precision of the redetermined sound velocity is less than a predetermined precision, and the sound velocity of this position is redetermined, and the assessment of the precision of the sound velocity is repeated again until the precision of the sound velocity is the predetermined precision or more.

Preferably, the sound velocity is determined at a plurality of positions inside the inspection object and the precision of the sound velocity is assessed for each position.

Preferably, the assessment of the precision of the sound velocity is performed using at least one of variation in the sound velocity, standard deviation in the sound velocity, a difference between a maximum value and a minimum value of the sound velocity, and an average value of the sound velocity.

The invention further provides a computer-readable recording medium that records a program making a computer execute the steps of: making a probe, in which a plurality of elements are arranged and which transmit an ultrasonic beam, receive ultrasonic echoes reflected by an inspection object, and output an analog element signal according to the received ultrasonic echoes, perform transmission of the ultrasonic beam a plurality of times so as to each form a predetermined transmission focus point using the plurality of elements and outputting of an analog element signal from the plurality of elements corresponding to the individual transmission of the ultrasonic beam;

analog-to-digital converting the analog element signal into first element data which is a digital element signal;

generating second element data corresponding to any one of a plurality of the first element data; and determining the sound velocity inside the inspection object using the second element data.

In the computer-readable recording medium that records the program, preferably, in the outputting of the analog element signal from the plurality of elements, the probe is made perform transmission of the ultrasonic beam a plurality of times, changing at least one of a center element and a transmission direction of the ultrasonic beam.

Preferably, in the generating of the second element data, the second element data is generated using at least one of a plurality of the first element data obtained by transmission of the ultrasonic beam where the center element is different to each other and a plurality of the first element data obtained by transmission of the ultrasonic beam where the transmission direction is different to each other.

Preferably, in the generating of the second element data, the second element data is generated from a plurality of the first element data obtained by transmission of the ultrasonic beam where transmission regions overlap.

Preferably, in the generating of the second element data, the second element data is generated by superimposing a plurality of the first element data according to a reception time at which the elements received the ultrasonic echoes and positions of the elements.

According to the invention, it is possible to accurately determine the sound velocity in all locations in an inspection object in an ultrasound diagnosis even without performing transmission and reception of ultrasonic waves corresponding to a large number of focus points in the depth direction. Therefore, according to the invention, it is possible to generate an ultrasonic image with high image quality on which a proper reception focusing process is performed using an accurate sound velocity without decreasing the frame rate.

BRIEF DESCRIPTION OF THE DRAWINGS

FIG. 2 is a conceptual diagram for describing an example of a reception focusing process in the ultrasound diagnostic apparatus depicted in FIG. 1.

FIG. 3 is a block diagram conceptually illustrating an example of a configuration of an element data processor of the ultrasound diagnostic apparatus depicted in FIG. 1.

FIG. 4A and FIG. 4C are conceptual diagrams for describing transmission and reception of ultrasonic waves using an ideal ultrasonic beam, and FIG. 4B and FIG. 4D are respective conceptual diagrams illustrating element data obtained by the transmission and reception of ultrasonic waves.

FIG. 5A and FIG. 5C are conceptual diagrams for describing the ultrasound transmission and reception according to an actual ultrasonic beam, and FIG. 5B and FIG. 5D are respective conceptual diagrams illustrating element data obtained by the transmission and reception of ultrasonic waves.

FIGS. 7A to 7C and FIGS. 7D to 7F are conceptual diagrams for describing element data of a true signal and ghost element data respectively, the delay times thereof, and states where the element data are superimposed, FIG. 7G is a conceptual diagram for describing states where element data corresponding to a plurality of elements are superimposed, and FIG. 7H is a conceptual diagram for describing the results of superimposing the element data in FIG. 7G.

FIG. 11 is a flow chart for describing another example of a sound velocity determining method of the ultrasound diagnostic apparatus depicted in FIG. 1.

DETAILED DESCRIPTION OF THE INVENTION

Below, detailed description will be given of the ultrasound diagnostic apparatus, the sound velocity determining method, and the recording medium of the invention based on suitable embodiments illustrated in the accompanying drawings.

Figure 1:
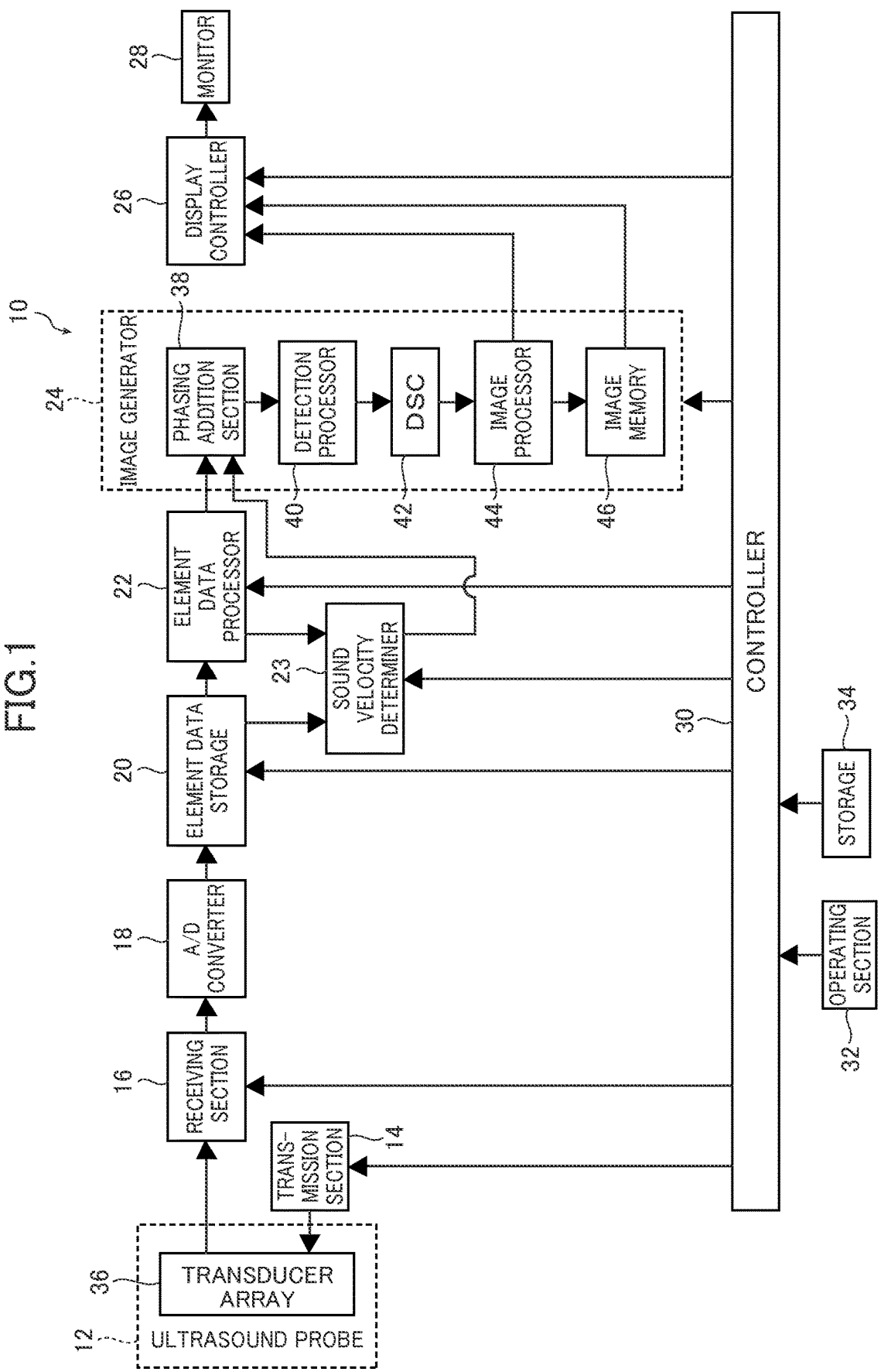
FIG. 1 is a block diagram conceptually illustrating an example of a configuration of an ultrasound diagnostic apparatus of the invention.

FIG. 1 is a block diagram conceptually illustrating an example of an ultrasound diagnostic apparatus of the invention which implements a sound velocity determining method of the invention.

As illustrated in FIG. 1, an ultrasound diagnostic apparatus 10 has an ultrasound probe 12, a transmission section 14 and a receiving section 16 connected with the ultrasound probe 12, an analog-to-digital (A/D) converter 18, an element data storage 20, an element data processor 22, a sound velocity determiner 23, an image generator 24, a display controller 26, a monitor 28, a controller 30, an operating section 32, and a storage 34.

In the example in the diagram, the transmission section 14, the receiving section 16, the A/D converter 18, the element data storage 20, the element data processor 22, the sound velocity determiner 23, the image generator 24, the display controller 26, the monitor 28, the controller 30, the operating section 32, and the storage 34 configure the apparatus main body of the ultrasound diagnostic apparatus 10.

The ultrasound probe 12 is a known ultrasound probe used in a normal ultrasound diagnostic apparatus.

The ultrasound probe 12 (hereinafter, referred to as the probe 12) has a transducer array 36 in which ultrasound transducers are one-dimensionally or two-dimensionally arranged.

When taking an ultrasound image of an inspection object (hereinafter, referred to as a subject), the ultrasound transducers each transmit ultrasonic beams to the subject in accordance with a driving signal supplied from the transmission section 14, receive ultrasonic echoes reflected by the subject, and output a reception signal according to the strength of the received ultrasonic waves.

Each ultrasound transducer is configured by an oscillator where electrodes are formed at both ends of a piezoelectric body formed of, for example, a piezoelectric ceramic represented by lead zirconate titanate (PZT), a polymer piezoelectric element represented by polyvinylidene fluoride (PVDF), a piezoelectric single crystal represented by lead magnesium niobate-lead titanate solid solution (PMN-PT), or the like.

When a pulsed or continuous wave voltage is applied to the electrodes of the oscillator, the piezoelectric body expands and contracts according to the applied voltage and pulsed or continuous ultrasonic waves are generated from each oscillator. In addition, the ultrasonic waves generated from each of the oscillators converge to be combined (that is, transmission focusing is performed on the ultrasonic waves) at set focus points according to a driving delay of each of the oscillators, thereby forming an ultrasonic beam.

In addition, the oscillators expand and contract due to ultrasonic echoes reflected inside the subject being incident thereto and electric signals are generated according to the size of the expansion and contraction. The electric signals are output to the receiving section 16 as the reception signal.

The transmission section 14 has, for example, a plurality of pulsars and supplies a driving signal (applies a driving voltage) to each of the ultrasound transducers (oscillators) of the probe 12.

Based on a transmission delay pattern selected by the controller 30, the transmission section 14 performs transmission focusing for adjusting a delay amount (an application timing of a driving voltage) of a driving signal so as to form an ultrasonic beam with an object of converging ultrasonic waves transmitted by a predetermined number (a plurality) of ultrasound transducers at set focus points, and supplies the driving signal to the ultrasound transducers. Here, the transmission delay pattern may be corrected according to an ambient sound velocity to be described below.

Due to this, the ultrasonic beam which is the object is transmitted from the probe 12 (the transducer array 36) to the subject.

According to a control signal from the controller 30, the receiving section 16 receives reception signals output by a predetermined number (a plurality) of ultrasound transducers corresponding to a single ultrasonic beam transmission, and supplies the result to the A/D converter 18 after carrying out a predetermined process such as amplification.

Here, the method of transmitting and receiving the ultrasonic waves in the ultrasound diagnostic apparatus 10 of the invention is basically the same as for a known ultrasound diagnostic apparatus.

Accordingly, in a single transmission and reception of ultrasonic waves (the transmission of one ultrasonic beam and the reception of ultrasonic echoes corresponding to this transmission), neither the number (the number of transmission openings) of ultrasound transducers which generate the ultrasonic waves nor the number (the number of reception openings) of ultrasound transducers (where the receiving section 16 receives the reception signal) which receive the ultrasonic waves is limited as long as there is more than one of each. In addition, in a single transmission and reception, the number of openings may be the same or different in the transmission and the reception.

In addition, with ultrasonic beams adjacent in at least the azimuth direction (the arrangement direction of the ultrasound transducers), when transmission regions overlap, neither the number of times (number of sound rays) of the transmission and reception of the ultrasonic waves for forming one ultrasound image nor the intervals (that is, the density of the scanning lines/sound rays) of the ultrasound transducers (center elements) in the center of the transmission and reception is limited. Accordingly, the transmission and reception of the ultrasonic waves may be performed with all of the ultrasound transducers corresponding to the region scanned with ultrasonic waves as the center elements, or the transmission and reception of the ultrasonic waves may be performed with ultrasound transducers at predetermined intervals, such as every two transducers or every four transducers, as the center elements.

The A/D converter 18 A/D converts the analog reception signal supplied from the receiving section 16 into element data (first element data) which is a digital reception signal.

The A/D converter 18 supplies the A/D converted element data to the element data storage 20.

The element data storage 20 sequentially stores the element data supplied from the A/D converter 18. In addition, the element data storage 20 stores information (for example, the depth of the reflection position of the ultrasonic waves, the density of the scanning lines, or a parameter indicating a visual field width) relating to the frame rate input from the controller 30 in association with each of the element data.

Preferably, the element data storage 20 stores all of the element data corresponding to at least one ultrasound image (an ultrasound image of one frame) and does not erase the element data of the ultrasound image before display or during display at least until the display of the ultrasound image is finished.

The element data processor 22 is a feature of the invention and generates processed element data (second element data) corresponding to each of the element data by superimposing the element data.

Specifically, under the control of the controller 30, the element data processor 22 superimposes the element data out of the element data stored in the element data storage 20 and obtained by a predetermined number (a plurality) of ultrasonic beam transmissions for which the ultrasound transducers in the center (the elements in the center (center elements)) are different and the transmission regions of the ultrasonic beams overlap, according to the time at which each of the ultrasound transducers receives the ultrasonic echoes and the positions of the ultrasound transducers, thereby generating processed element data corresponding to the element data (element data of an element of interest to be described below).

The element data processor 22 sends the generated processed element data to the sound velocity determiner 23 and the image generator 24.

The sound velocity determiner 23 determines the sound velocity (the ambient sound velocity) of ultrasonic waves in a subject using the processed element data generated by the element data processor 22.

Detailed description will be given below of the element data processor 22, the processed element data, the sound velocity determiner 23, and the ambient sound velocity.

The image generator 24 generates reception data (sound ray signal) from the processed element data supplied from the element data processor 22 under the control of the controller 30 and generates an ultrasound image from this reception data.

The image generator 24 has a phasing addition section 38, a detection processor 40, a DSC 42, an image processor 44, and an image memory 46.

The phasing addition section 38 performs a reception focusing process by carrying out matching addition on the processed element data generated by the element data processor 22, and generates reception data.

As described above, in the transducer array 36 of the probe 12, a plurality of elements (ultrasound transducers) is one-dimensionally or two-dimensionally arranged. Accordingly, the distance to one reflection point in the subject is different for each of the ultrasound transducers. Therefore, even with ultrasonic echoes reflected at the same reflection point, the time for the ultrasonic echoes to arrive at each of the ultrasound transducers is different. According to a reception delay pattern selected by the controller 30, the phasing addition section 38 delays each of the processed element data by an amount corresponding to the difference (the delay time) in the arrival time of the ultrasonic echoes for each of the ultrasound transducers, and carries out matching addition on the processed element data to which the delay time is added, thereby digitally performing a reception focusing process and generating reception data.

The phasing addition section 38 supplies the generated reception data to the detection processor 40.

Here, in a case where the sound velocity (the ambient sound velocity) of the ultrasonic waves in the subject is determined by the sound velocity determiner 23 and supplied to the phasing addition section 38, the phasing addition section 38 performs the reception focusing process by correcting the delay time, the reception delay pattern, or the like using the ambient sound velocity.

Here, in a case where the ambient sound velocity is not determined, the phasing addition section 38 performs the reception focusing process with a known method in which a reception delay pattern is used.

FIG. 2 illustrates an example of the reception focusing process using the ambient sound velocity.

Here, FIG. 2 illustrates a case of a linear probe where the plurality of ultrasound transducers of the probe 12 is arranged in a row in the left and right direction in the diagram. However, the concept may be similarly applied even in the case of a convex probe where only the probe shape is different.

When the width of each of the ultrasound transducers in the azimuth direction is taken to be L, the distance up to the n-th ultrasound transducer from the ultrasound transducer in the center of the azimuth direction toward the end section is nL.

As illustrated in the same diagram, when the reflection point of the ultrasonic waves is taken to be at a position at a distance (depth) d, which is perpendicular to the arrangement direction, from the center ultrasound transducer, the distance (length) $d_n$ between the n-th ultrasound transducer and the reflection point is calculated using the formula (1).

$$d_n = ((nL)^2 + d^2)^{1/2} \tag{1}$$

Accordingly, using the ambient sound velocity Va, a time $t_n$ for the ultrasonic echoes from the reflection point to arrive at (be received by) the n-th ultrasound transducer is calculated using the formula (2).

$$t_n = d_n/Va = ((nL)^2 + d^2)^{1/2}/Va \tag{2}$$

As described above, the distance between the ultrasound transducers and the reflection point is different for each ultrasound transducer. Therefore, in the case of this example, as illustrated in the graph at the top of the same diagram, the arrival time $t_n$ of the ultrasonic echoes is longer for the ultrasound transducers toward the end section sides in the arrangement direction.

Specifically, when the time until the ultrasonic waves are received by the center ultrasound transducer from the reflection point is taken to be $t_1$, the ultrasonic waves received by the n-th ultrasound transducer are delayed by the time $\Delta t = t_n - t_1$ with respect to the ultrasonic waves received by the center ultrasound transducer. In the present example, the delay time $\Delta t$ is a reception delay pattern.

The phasing addition section 38 performs phasing addition for the reception data corresponding to each of the ultrasound transducers using the delay time represented by the time $\Delta t$ described above and performs a reception focusing process.

Here, in the invention, the reception focusing process according to the ambient sound velocity is not limited to this method and it is possible to use various known methods.

For example, the controller 30 may select a reception delay pattern according to the ambient sound velocity and supply the control signal according thereto to the phasing addition section 38. Alternatively, the controller 30 may correct the reception delay pattern according to the ambient sound velocity and supply the control signal according to the corrected reception delay pattern to the phasing addition section 38. Alternatively, the phasing addition section 38 may correct the control signal supplied from the controller 30 according to the ambient sound velocity and perform the reception focusing process.

After carrying out correction of the attenuation due to the distance according to the depth of the reflection position of the ultrasonic waves on the reception data generated by the phasing addition section 38, the detection processor 40 generates B mode image data which is tomographic image information (brightness image information) in the subject by carrying out an envelope detection process.

The digital scan converter (DSC) 42 converts (raster converts) the B mode image data generated by the detection processor 40 into image data corresponding to a normal television signal scanning system.

The image processor 44 carries out various necessary image processes such as a gradation process on the B mode image data input from the DSC 42 to create B mode image data for display. The image processor 44 outputs the image processed B mode image data to the display controller 26 for display and/or stores the image processed B mode image data in the image memory 46.

The image memory 46 is a known storage (a storage medium) which stores the B mode image data processed by the image processor 44. The B mode image data stored in the image memory 46 is read out to the display controller 26 for display on the monitor 28 as necessary.

The display controller 26 uses the B mode image data on which the predetermined image process is carried out by the image processor 44 to display an ultrasound image on the monitor 28.

The monitor 28, for example, includes a display apparatus such as an LCD and displays an ultrasound image under the control of the display controller 26.

The controller 30 controls each section of the ultrasound diagnostic apparatus 10 on the basis of instructions input from the operating section 32 by an operator.

In addition, the controller 30 supplies various types of information input by an operator using the operating section 32 to necessary units. For example, in a case where information necessary for calculating the delay time used in the element data processor 22 and the phasing addition section 38 of the image generator 24 and information necessary for element data processing in the element data processor 22 are input by the operating section 32, the information is supplied to each section such as the transmission section 14, the receiving section 16, the element data storage 20, the element data processor 22, the image generator 24, and the display controller 26 as necessary.

The operating section 32 is for the operator to perform an input operation and can be formed of a keyboard, a mouse, a trackball, a touch panel, or the like.

In addition, the operating section 32 is provided with an input function for the operator to input various types of information as necessary. For example, the operating section 32 is provided with an input function for inputting information of the probe 12 (the ultrasound transducer); information relating to the generation of the processed element data such as the transmission opening and the reception opening in the probe 12 (the transducer array 36), the number of element data to be superimposed, or the generation method; the focus point position of the ultrasonic beam; and the like.

The above are input, for example, by selecting the photograph site (the examination site), selecting the image quality, selecting the depth of the ultrasound image to be photographed, and the like.

The storage 34 stores information necessary for the controller 30 to operate and control the ultrasound diagnostic apparatus such as information relating to an operation program for the controller 30 to execute control of each section of the ultrasound diagnostic apparatus 10, the transmission delay pattern and the reception delay pattern, and the generation of processed element data; information on the probe 12 input from the operating section 32; information on the transmission opening, the reception opening, and the focus point position.

In the storage 34, it is possible to use a known recording medium such as a hard disk, a flexible disk, an MO, an MT, a RAM, a CD-ROM, or a DVD-ROM.

Here, in the ultrasound diagnostic apparatus 10, the element data processor 22, the sound velocity determiner 23, the phasing addition section 38, the detection processor 40, the DSC 42, the image processor 44, the display controller 26, and the like are configured by a CPU and an operation program causing the CPU to execute various processes. However, in the invention, these units may be configured by a digital circuit.

As described above, the element data processor 22 generates processed element data by superimposing element data out of the element data (the unprocessed element data) stored in the element data storage 20 and obtained by a predetermined number (a plurality) of ultrasonic beam transmissions, for which the center ultrasound transducers (the center elements) are different and the transmission regions of the ultrasonic beams overlap, according to the time of being received by each ultrasound transducer and the position of the ultrasound transducers.

Here, in the following description, the ultrasound transducers are also referred to simply as "elements".

FIG. 3 is a block diagram conceptually illustrating the configuration of the element data processor 22.

As illustrated in FIG. 3, the element data processor 22 has a delay time calculator 48 and a superimposition processor 49.

The delay time calculator 48 acquires beforehand necessary information input from the operating section 32 or stored in the storage 34 after being input from the operating section 32 relating to the probe 12 (the ultrasound transducer (element)), focus point positions of the ultrasonic beams, the transmission opening and the reception opening of the probe 12, and the like.

In addition, the delay time calculator 48 calculates the delay time of the ultrasonic echoes received by the elements of the reception openings, that is, the element data, based on the geometric positions of the elements of the transmission openings which oscillate the ultrasonic waves in order to transmit (generate) the ultrasonic beams and the elements of the reception openings which receive the ultrasonic echoes from the subject.

The superimposition processor 49 reads out element data (element data obtained by ultrasonic beams for which the center elements are different and the transmission regions overlap (two or more element data generated for each of two or more target regions)) to be superimposed from the element data stored in the element data storage 20 based on information relating to the number of element data to be superimposed and the element data process such as a superimposition process method input from the operating section 32 or stored in the storage 34 after being input from the operating section 32.

Furthermore, based on the delay time corresponding to each of the element data calculated by the delay time calculator 48, the superimposition processor 49 superimposes two or more element data according to the reception time, that is, by matching the time and by matching the received absolute positions of the elements of the probe, thereby generating the processed element data.

Below, detailed description will be given of the processing of the element data performed by the element data processor 22.

Firstly, description will be given of a relationship between ultrasonic beams from the transmission elements and element data obtained by the reception elements in a case where, in the ultrasound probe 12, the ultrasonic beams are transmitted to the subject from the transmission opening, that is, the element which sends out the ultrasonic waves in order to transmit the ultrasonic beams (hereinafter, simply referred to as the transmission element), and the element data is obtained by receiving the ultrasonic echoes generated by interaction with the subject in the reception opening, that is, in the element which receives the ultrasonic echoes (hereinafter, simply referred to as the reception element).

As an example, as illustrated in FIG. 4A, the ultrasonic beams are transmitted with three elements 52c to 52e as transmission elements and the ultrasonic echoes are received with seven elements 52a to 52g as reception elements. Next, as illustrated in FIG. 4C, the ultrasonic beams are transmitted with three elements 52d to 52f as transmission elements by moving (hereinafter, also referred to as shifting) the elements by one element in the azimuth direction and each of the element data is acquired by receiving the ultrasonic echoes with seven elements 52b to 52 h as the reception elements.

That is, the center element (the element in the center) is the element 52d in the example illustrated in FIG. 4A and the center element is the element 52e in the example illustrated in FIG. 4C.

Now, an ideal case will be considered in which ultrasonic beams 56 transmitted to the inspection object region including a reflection point 54 are converged at a focus point 58 and narrowed to the element intervals or less.

As illustrated in FIG. 4A, when ultrasonic beams 56 are transmitted from the elements 52c to 52e which are transmission elements with the element 52d directly above (on a straight line linking the reflection point and the focus point) the reflection point 54 as the center element and the element data is acquired by receiving the ultrasonic echoes in the elements 52a to 52g which are the reception elements, the focus point 58 of the ultrasonic beam 56 is on a straight line linking the element 52d which is the center element and the reflection point 54. In such a case, since the ultrasonic beam 56 is transmitted up to the reflection point 54, the ultrasonic echoes reflected from the reflection point 54 are generated.

The ultrasonic echoes from the reflection point 54 are received in the elements 52a to 52g which are the reception elements after passing through a receiving path 60 extending at a predetermined angle and the element data 52 as illustrated in FIG. 4B is obtained by the elements 52a to 52g. Here, in FIG. 4B, the vertical axis represents the time and the horizontal axis represents the position (the position of the elements) in the azimuth direction (the same applies to FIG. 4D) corresponding to FIG. 4A.

In contrast, as shown in FIG. 4C, in a case where the center element is shifted by the amount of one element, the element 52e next to the element 52d directly above the reflection point 54 becomes the center element.

The ultrasonic beam 56 is transmitted from the elements 52d to 52f which are transmission elements with the element 52e as the center element and the ultrasonic echoes are received in the elements 52b to 52h which are the reception elements. At this time, in the same manner, when the ultrasonic beam 56 is ideal, the reflection point 54 is not present in the transmission direction of the ultrasonic beam 56, that is, on a straight line linking the center element 52e and the focus point 58. Accordingly, the ultrasonic beam 56 is not transmitted to the reflection point 54.

Therefore, the ultrasonic echoes reflected from the reflection point 54 are not generated and the elements 52b to 52h which are reception elements do not receive the ultrasonic echoes, thus, as illustrated in FIG. 4D, the reflected signal from the reflection point 54 is not obtained (the signal strength of the element data is "0").

However, since the actual ultrasonic beam is diffused after being converged at the focus point 58 as in an ultrasonic beam 64 illustrated in FIGS. 5A and 5C, the width is wider than the element interval.

Here, similar to FIG. 4A, in a case where the ultrasonic beam 64 is transmitted with the elements 52c to 52e as the transmission elements and the element 52d directly above the reflection point 54 as the center element as in FIG. 5A, even when the ultrasonic beam 64 is wide, the focus point 58 is on a straight line linking the element 52d and the reflection point 54. Accordingly, the ultrasonic beam 64 is reflected at the reflection point 54 and ultrasonic echoes are generated.

As a result, in the same manner as the case of FIG. 4A, the ultrasonic echoes from the reflection point 54 are received in the elements 52a to 52g which are the reception elements after passing through a receiving path 60 which widens at a predetermined angle, and, similarly, true element data 66 as illustrated in FIG. 5B is obtained.

Next, in the same manner as FIGS. 4A to 4D, as illustrated in FIG. 5C, the ultrasonic beam 64 is transmitted by shifting the center element by one element with the adjacent element 52e as the center element and the elements 52d to 52f as the transmission elements and the ultrasonic echoes are received with the elements 52b to 52h as the reception elements. Even in such a case, since the ultrasonic beam 64 is wide, even when the reflection point 54 is not present in the transmission direction of the ultrasonic waves, that is, on a straight line linking the element 52e which is the center element and the focus point 58, the ultrasonic beam 64 is transmitted to (arrives at) the reflection point 54.

Therefore, ultrasonic echoes which did not exist originally or so-called ghost reflected echoes are generated in the transmission direction of the ultrasonic beam from the reflection point 54. The ghost reflected echoes from the reflection point 54 are received in the elements 52b to 52h which are reception elements after passing through the receiving path 60 which widens at a predetermined angle as illustrated in FIG. 5C. As a result, ghost element data 68 as illustrated in FIG. 5D is obtained by the elements 52b to 52h.

In this manner, the ghost element data 68 is a cause of the precision of the ultrasound image generated from the element data decreasing.

The element data processor 22 calculates the delay time corresponding to the element data in the delay time calculator 48 and the superimposition processor 49 superimposes two or more element data according to the delay time and the absolute position of the elements, whereby processed element data which is element data with high precision in which the ghost element data is attenuated by emphasizing the true element data is generated.

As described above, the delay time calculator 48 calculates the delay time of the element data received in each of the elements of the reception elements (reception openings).

That is, the propagation distance of the ultrasonic beam 64 illustrated in FIG. 5C is the sum of the transmission path where the ultrasonic beam 64 reaches the reflection point 54 from the element 52e which is the center element via the focus point 58 and the receiving path where the ghost reflected echoes from the reflection point 54 reach each of the elements 52b to 52h which are the reception elements.

The propagation distance of the ultrasonic beam 64 illustrated in FIG. 5C is longer than the propagation distance of the ultrasonic beam 64 illustrated in FIG. 5A, that is, the sum of the transmission path where the ultrasonic beam 64 reaches the reflection point 54 from the center element 52d via the focus point 58 and the receiving path where the true reflected echoes from the reflection point 54 reach the elements 52a to 52g which are the reception elements.

Therefore, the ghost element data 68 as illustrated in FIG. 5D is delayed with respect to the true element data 66 as illustrated in FIG. 5B.

In the delay time calculator 48 of the element data processor 22, the time difference between the true element data and the ghost element data, that is, the delay time is calculated from the sound velocity, the transmission elements, the focus point of the ultrasonic beam, the reflection point of the subject, and the geometric arrangement of the reception elements.

Accordingly, in the calculation of the delay time, information such as the shape of the probe 12 (the element interval, the probe being linear, convex, or the like), the sound velocity, the position of the focus point, the transmission opening, and the reception opening is necessary. In the delay time calculator 48, the information input by the operating section 32 or stored in the storage 34 is acquired to calculate the delay time. Here, the sound velocity may use a fixed value (for example, 1540 m/sec), may use a sound velocity (the ambient sound velocity) determined by the sound velocity determiner 23 to be described below, or may be input by the operator.

It is possible for the delay time to be calculated from the difference in the propagation time calculated according to the sound velocity and the total length (propagation distance) of the transmission path of the ultrasonic beam from the transmission element to the reflection point via the focus point and the receiving path of true reflected ultrasonic echoes or the ghost reflected signal from the reflection point up to the reception elements, which is calculated from the geometric arrangement of, for example, the transmission elements, the focus point of the ultrasonic beam, the reflection point of the subject, and the reception elements.

Figure 6A:
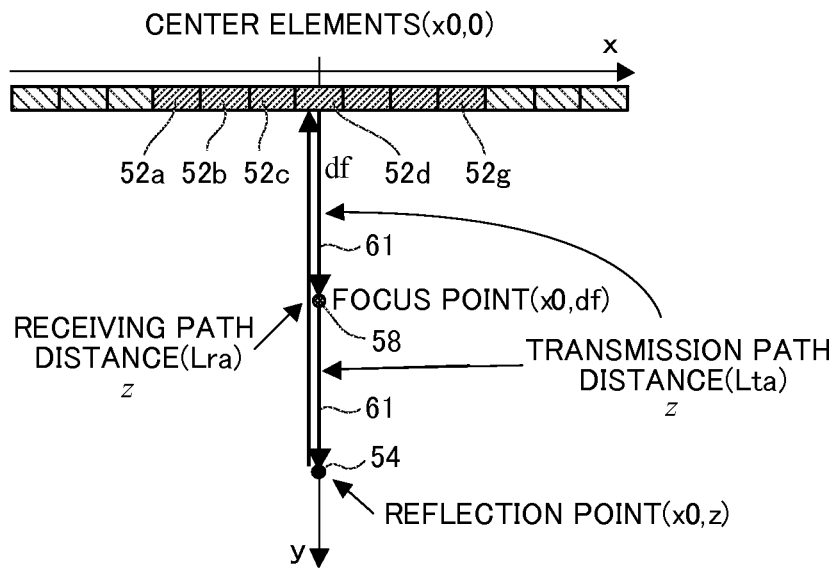
FIG. 6A and FIG. 6B are conceptual diagrams for describing a path of a sound wave in a case where the transmission and reception of ultrasonic waves is performed with respect to the same reflection point using center elements which are different from each other.
Figure 6B:
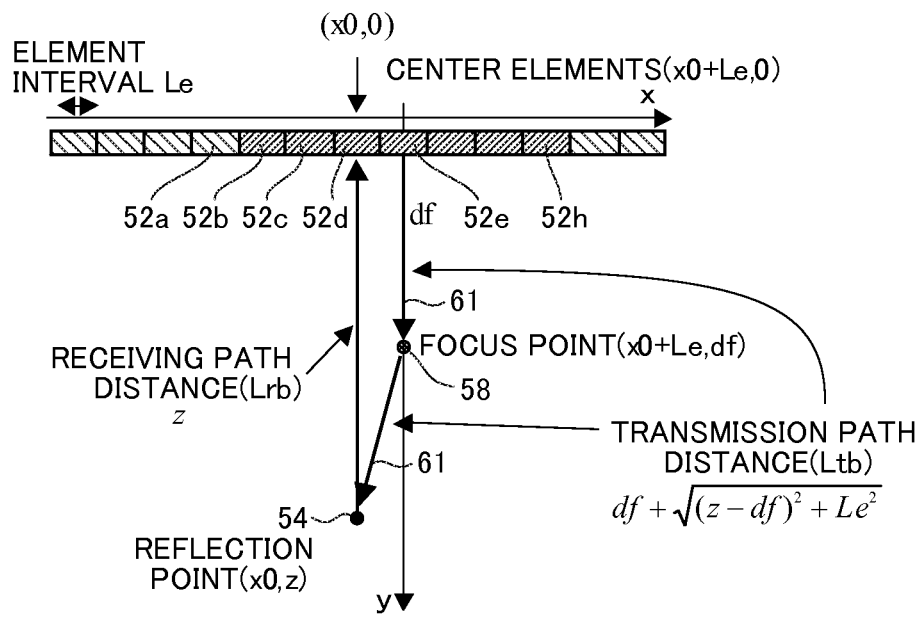

In the invention, for example, as illustrated in FIG. 6A and FIG. 6B, it is possible to determine the length of the transmission path and the receiving path of the ultrasonic beam in the case of the true ultrasonic echoes and the ghost reflected echoes. Here, in FIG. 6, the x direction is the azimuth direction and the y direction is the depth direction.

In addition, in FIG. 6A, the transmission and reception of the ultrasonic waves is performed in the same manner as in FIG. 5A and, in FIG. 6B, the transmission and reception of the ultrasonic waves is performed in the same manner as in FIG. 5C.

In the case of the true ultrasonic echoes, as illustrated in FIG. 6A (FIG. 5A), the element 52d which is the center element, the focus point 58, and the reflection point 54 are positioned on a straight line (the positions are matched in the azimuth direction). That is, the focus point 58 and the reflection point 54 are positioned directly below the center element 52d.

Accordingly, when the position of the element 52d which is the center element is taken to be coordinates (x0, 0) which are two dimensional x-y coordinates, the x coordinate of the focus point 58 and the reflection point 54 is also "x0". Below, the position of the focus point 58 in the transmission is taken to be coordinates (x0, df), the position of the reflection point 54 is taken to be coordinates (x0, z), and the interval of the elements is taken to be Le.

At this time, it is possible for the length (transmission path distance) Lta of a transmission path 61 of the ultrasonic beam from the element 52d which is the center element to the reflection point 54 via the focus point 58 and the length (the receiving path distance) Lra of the receiving path 60 of the true reflecting ultrasonic echoes from the reflection point 54 to the element 52d to be calculated using Lta=Lra=z.

Accordingly, in the case of the true ultrasonic echoes, the propagation distance Lua of the ultrasonic echoes is Lua=Lta+Lra=2z.

Next, as illustrated in FIG. 6B, by shifting (shifting in the direction to the right in the diagram) the transmitting element and the reception element by one element in the x direction (the azimuth direction), transmission and reception are performed with the element 52e as the center element. As illustrated in FIG. 5C, in this case, the echoes reflected at the reflection point 54 are the ghost reflected echoes.

The reflection point 54 is positioned directly below (at the same position in the azimuth direction) the element 52d. Accordingly, as illustrated in FIG. 6B, in the transmission and the reception, the positions of the element 52e which is the center element and the reflection point 54 in the x direction are shifted in the x direction by one element, that is, by Le.

Since the coordinates of the element 52d whose position matches the reflection point 54 in the x direction are (x0, 0), the coordinates of the element 52e which is the center element become (x0+Le, 0) and the coordinates of the focus point 58 in the transmission become (x0+Le, df). Here, as described above, the coordinates of the reflection point 54 are (x0, z).

Accordingly, it is possible for the length (the transmission path distance) Ltb of the transmission path 61 of the ultrasonic beam from the element 52e which is the center element to the reflection point 54 via the focus point 58 to be calculated by $Ltb=df+\sqrt{\{(z-df)^2+Le^2\}}$. On the other hand, it is possible for the length (the receiving path distance) Lrb of the receiving path 60 of the ghost reflected signal from the reflection point 54 to the element 52d directly below (at the same position in the x direction=azimuth direction) to be calculated using the Lrb=z.

Accordingly, the propagation distance Lub of the ultrasonic waves in the case of the ghost reflected echoes is $Lub=Ltb+Lrb=df+\sqrt{\{(z-df)^2+Le^2\}}+z$.

In this manner, a value where the propagation distance Lua of the ultrasonic waves which is the total of the distance Lta of the transmission path 61 and the distance Lra of the receiving path 60 determined by the geometric arrangement illustrated in FIG. 6A is divided by the sound velocity is the propagation time of the true ultrasonic echoes. In addition, a value where the propagation distance Lub of the ultrasonic waves which is the total of the distance Ltb of the transmission path 61 and the distance Lrb of the receiving path 60 determined by the geometric arrangement illustrated in FIG. 6B is divided by the sound velocity is the propagation time of the ghost reflected echoes.

The delay time is determined from the difference between the propagation time of the true ultrasonic echoes when the x coordinates of the reflection point 54 and the center element are matched and the propagation time of the ghost reflected echoes when the x coordinates of the reflection point 54 and the center element are shifted by a single element interval at a time.

Here, the geometric model of FIG. 6A and FIG. 6B is a model where the transmission path 61 goes via the focus point 58; however, the invention is not limited thereto, and, for example, may be a path arriving directly at the reflection point 54 without going via the focus point 58.

In addition, the geometric model of FIG. 6A and FIG. 6B is for the case of a linear probe; however, without being limited thereto, it is possible to perform the geometric calculation in the same manner from the shape of the probe even with other probes.

For example, in the case of a convex probe, it is possible to carry out the calculation in the same manner by setting the geometric model using the radius of the probe and angle of the element interval.

In addition, in the case of a steering transmission, it is possible to calculate the delay time of the true element data and the ghost element data of the surroundings thereof from the positional relationship between the transmission elements and the reflection points using a geometric model taking information such as the transmission angle into consideration.

Furthermore, without being limited to a method of calculating the delay time according to a geometric model, by determining the delay time for every measuring condition from the measuring results of measuring the high brightness reflection point in accordance with the measuring conditions of the apparatus in advance and storing the delay times in the apparatus, the delay time for the same measuring conditions may be read out.

Figure 6C:
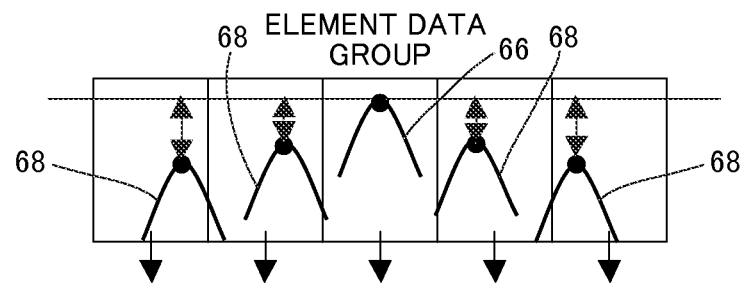
FIG. 6C is a conceptual diagram for describing element data obtained by a plurality of elements.

FIG. 6C illustrates the true element data 66 and the ghost element data 68.

In FIG. 6C, the center in the azimuth direction is the true element data 66, that is, element data (element data where the element 52d is taken to be the center element in the example in the diagram) obtained by transmission and reception where the positions of the center element and the reflection point 54 match in the x direction. In addition, both sides of the center are ghost element data, that is, element data (element data where the element data 52c or the element 52e is taken to be the center element in the example in the diagram) obtained by transmission and reception where the positions of the center element and the reflection point 54 do not match in the x direction.

Figure 6D:
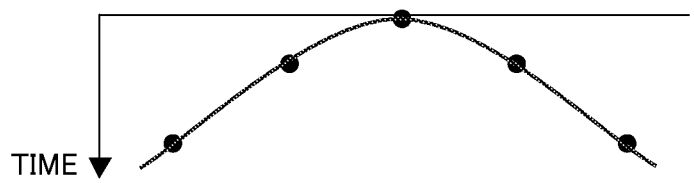
FIG. 6D is a conceptual diagram for describing each of the delay times of the element data depicted in FIG. 6C.

In addition, FIG. 6D illustrates an example of the delay time of the ghost element data 68 with respect to the true element data 66 obtained by the geometric calculation described above. Centering on the true element data 66, the element data 68 of the ghost signal indicates that the time is symmetrically delayed in the x direction, that is, the azimuth direction.

Here, in this manner, it is also possible for the delay time calculated in the delay time calculator 48 of the element data processor 22 to be used in the delay correction in the phasing addition section 38.

As will be described in detail below, in the invention, by superimposing element data, which is obtained by the transmission of the ultrasonic beam where at least a part of the ultrasonic beam overlap and for which the center element is different, on element data, which is obtained by the transmission (the transmission and reception of the element of interest) of an ultrasonic beam where a certain element of interest is the center element, by matching the reception time of the ultrasonic echoes and the position of the elements, the processed element data (second element data) of the element of interest is generated (the element data of the element of interest is rebuilt).

In FIGS. 6A to 6D, the reflection point 54 indicates the position (the output position of the element data) of a certain sampling point positioned directly below the element of interest (at the same position in the azimuth direction or on a straight line linking the element of interest and the focus point). In the invention, the transmission and reception path to the sampling point in the transmission and reception of the element of interest is regarded as the transmission and reception path of the true element data and the transmission and reception path to the same sampling point in the transmission and reception (the transmission and reception from the surrounding elements) of the ultrasonic waves where the center element is different is regarded as the ghost transmission and reception path. The superimposition is performed by calculating the delay time from the difference between both transmission paths and matching the time of the element data using the delay time. In other words, the delay time is calculated and the superimposition of the element data is performed assuming that element data obtained by the transmission and reception of the element of interest is the true element data and element data obtained by the transmission and reception where the center element is different is the ghost element data.

In the invention, the superimposition of the element data is performed by calculating the delay time with the same concept corresponding to all of the sampling points (the output position of all the element data) and the processed element data of each of the elements is generated.

Here, in fact, even when the positions of the sampling points (reflection points) are shifted in the azimuth direction (the x direction), the length of the receiving path (the receiving path distance Lrb) does not change. Accordingly, in relation to each of the elements of interest, the calculation of the delay times of the element data according to transmission and reception for which the center elements are different may be performed for every sampling point in the depth direction (the y direction).

In addition, it is not necessary to know which element data the true element data is in the superimposition process. That is, although described in detail with reference to FIGS. 7A to 7H below, in the superimposition process, the element data of the element of interest is automatically emphasized and remains when the element data is the true element data and the element data is cancelled when the element data is ghost element data. That is, in a case where the element data of the element of interest is the true element data, the signal is emphasized by matching the process according to the delay time and, in a case where the element data of the element of interest is the ghost element data, the signal is cancelled without matching the process according to the delay time.

Next, in the superimposition processor 49 of the element data processor 22 of the invention, the superimposition process of the element data is performed using the delay time calculated in the delay time calculator 48 in this manner.

Here, in the superimposition process in the superimposition processor 49, information on the superimposition processing method and the number of superimposition element data at the time of the superimposition is necessary; however, this information may be input using the operating section 32 in advance, or may be stored in the storage 34 in advance.

FIGS. 7A to 7H illustrate an example of the superimposition process performed in the superimposition processor 49. Here, the example illustrated in FIGS. 7A to 7H is of a case where the number of element data is five and the number of superimposition element data is three.

FIG. 7A displays five element data obtained by carrying out the transmission and reception of the ultrasonic waves five times lined up side by side. In addition, FIG. 7A represents a state where ultrasonic echoes are received after the ultrasonic beams are transmitted for each element data. The horizontal axis of each element data represents a reception element and displays the center element in the center in the transmission and reception of the ultrasonic beam in each of the element data. The vertical axis represents the reception time. In this example, transmission and reception of the ultrasonic waves is performed five times by shifting the center element by one element at a time, for example, in the above-described elements 52b to 52f or the like.

FIGS. 7A to 7H illustrate a state where one reflection point is present only directly below the center element in the center element data. That is, out of the five element data, the true ultrasonic echoes are received in the element data in the middle from the reflection point in the transmission and reception of the ultrasonic waves. That is, the element data in the middle is the true element data.

Regarding the two element data on both sides other than the element data in the middle, the reflection point is not present directly below the center element in the transmission and reception of the ultrasonic waves. However, due to the ultrasonic beam hitting the reflection point which is present directly below the transmission element of the element data in the middle according to the spread of the transmitted ultrasonic beam, the generated reflected echo element data, that is, the ghost element data bleeds through.

The further the ghost element data is separated from the true element data, the longer the propagation time of the ultrasonic waves up to the reflection point, thus the reception time for the ghost element data is longer than for the true element data. In addition, the position of the reception element where the ultrasonic echoes from the reflection point are first received is directly above the reflection point (an element whose position in the azimuth direction matches the reflection point).

Here, the horizontal axis of each of the element data in FIGS. 7A to 7H sets the center element during the transmission of the ultrasonic beam in the center. Accordingly, in the example illustrated in FIG. 7, since transmission is carried out by shifting the center element by one element for each of the element data, the absolute position of the elements in the azimuth direction in each element data is shifted by one element at a time. In other words, in the element data in the middle, the reception element which first receives the reflected signal from the reflection point is the center element; however, in both adjacent element data, the reception element is shifted by one element from the element data in the middle, the element data on the right side is shifted by one element to the left, and the element data on the left side is shifted one element to the right. Furthermore, the element data on both ends is shifted by two elements from the element data in the middle, the element data at the right end is shifted by two elements to the left, and the element data at the left end is shifted by two elements to the right. In this manner, not only is the reception time longer for the ghost signal than for the true signal, but shifting is also generated with respect to the direction of the reception elements.

FIG. 7B illustrates an example of the delay time of the reception time with respect to the element data in the middle of the five element data illustrated in FIG. 7A.

In the superimposition processor 49, in a case where the element data in the middle is set as the element data of the element of interest, the delay time correction is performed according to the number of element data to be superimposed (three elements in the example in the diagram) centering on the element data of the element of interest using the delay time illustrated in FIG. 7B. Also, by shifting each element data by one element in the azimuth direction at both sides in the example in the diagram according to the difference of the element position on the element of interest (difference with the position of the center element), that is, by matching the phases, unprocessed element data for three elements are superimposed and determined as one superimposition processed element data for the element data of the element of interest.

That is, in the present example, the processed element data of the element data of the element of interest is generated by superimposing the element data (hereinafter, also referred to as the element data of the adjacent element) obtained by transmission and reception of the ultrasonic waves where the element adjacent to the element of interest is the center element on the element data (hereinafter, also referred to as element data of the element of interest) obtained by the transmission and reception of the ultrasonic waves where the element of interest is the center element.

The superimposition processed element data of the element data of the element of interest obtained in this manner is illustrated in FIG. 7C.

As described above, the element data of the element of interest illustrated in FIG. 7A is true element data in which the reflection point is present directly below the center element (that is, the element of interest). In addition, the element data obtained by the transmission and reception of ultrasonic waves where an element adjacent to the element of interest is the center element is also ultrasonic echo data where the ultrasonic waves are incident on the reflection point and reflected.

Accordingly, when performing the phase matching by carrying out delay time correction and azimuth direction shifting on the element data of the elements adjacent at both sides of the element of interest, the element data of the adjacent element and the element data of the element of interest overlap at a high brightness position since the phases match as illustrated in FIG. 7C. Therefore, for example, when the element data are added, the element data value indicates a large value (high brightness value). For instance, the element data indicates an emphasized value (high brightness value) even when an average value is determined by averaging.

In contrast, FIG. 7D illustrates an example of a case with the same element data as FIG. 7A; however, the element data adjacent to the left of the element data in the middle is the element data of the element of interest. That is, this example illustrates a case of the transmission and reception of ultrasonic waves where an element for which the reflection point is not present directly below is the center element, in which the center element is the element of interest. Accordingly, the element data where the element is the center element is ghost element data.

FIG. 7E is the same as FIG. 7B and illustrates an example of the delay time of the reception time with respect to the element data of the element of interest of the five element data illustrated in FIG. 7A. That is, since FIG. 7A and FIG. 7D are of the same element data, the delay time of the reception time with respect to the element data of the element of interest of the five element data illustrated in FIG. 7D is also the same.

In the superimposition processor 49, the delay time correction is performed according to the number of element data to be superimposed (three elements in the example in the diagram) centering on the element data of the element of interest using the delay time illustrated in FIG. 7E (that is, the same as FIG. 7B). Also, by shifting each element data by one element in the azimuth direction at both sides in the example in the diagram according to the difference of the element position with the element of interest (difference with the position of the center element), three unprocessed element data are superimposed and determined as one superimposition processed element data for the element data of the element of interest.

The superimposition processed element data of the element data of the element of interest obtained in this manner is illustrated in FIG. 7F.

The element data of the element of interest illustrated in FIG. 7D is ghost element data. Therefore, even when phase matching is performed by performing delay time correction and azimuth direction shifting on the unprocessed element data of the adjacent element data on both sides of the element data of the element of interest, as illustrated in FIG. 7F, each element data of the adjacent element data and the element data of the element of interest do not overlap because the phases are not mutually matched. For this reason, since the phases do not match even when, for example, three element data are added, signals or the like where the phases are inverted cancel each other out, thus the added value is not large and, for example, a small value is indicated when the average value is determined by averaging.

In relation to the other element data, FIG. 7G illustrates an overlapping state of three adjacent element data for each of five element data in the example in the diagram as a result of performing the same delay time correction and azimuth direction shifting as for the element data of the element of interest. With respect to these, FIG. 7H illustrates the results after, for example, an addition process or an averaging process is carried out as the superimposition process.

As illustrated in FIG. 7H, in a case of element data where a center element where the reflection point is present directly below illustrated in FIG. 7A is the element of interest, the element data of the true signal is determined as superimposition processed element data having a high brightness value. In contrast, in all four element data of each of the two element data on both sides thereof, for the ghost element data, the element data where the phases do not match each other are added or averaged. Therefore, since the element data cancel each other out, the value of the ghost superimposition processed element data is lower than that of the superimposition processed element data having a high brightness value which is element data of a true signal, and it is possible to reduce the influence of the ghost element data on the true element data, or it is possible to reduce the influence thereof to a level which may be ignored.

That is, one or more of the element data which is obtained by transmission and reception of the ultrasonic waves for which the transmission regions of the ultrasonic beam overlap and for which the center elements are different are superimposed on element data (element data of the element of interest) where a certain element is set as the element of interest and which is obtained by transmission of an ultrasonic beam where this element of interest is the center element by carrying out time and azimuth direction position matching, and processed element data corresponding to the element data of the element of interest is generated. Due to this (in other words, by performing rebuilding (correction) of the element data of the element of interest using element data according to transmission and reception where at least a portion of the ultrasonic beam overlap and the center element is different), the brightness level of the true element data is increased and it is possible to decrease the ghost element data.

Therefore, as will be described below, according to the invention which performs determination of the sound velocity using the processed element data, it is possible to determine the sound velocity in the subject with high precision by eliminating the influence of the ghost and using equal element data in such a case that the focus points are linked at a large number of points on the sound ray to be transmitted, that is, element data (the reception data (ultrasound image data)) obtained by the transmission of the ultrasonic waves at multiple virtual focus points.

In addition, similarly, since it is possible to generate the ultrasound image with element data in such a case that the influence of the ghost is eliminated, that is, the focus points at all points on the sound ray are linked by performing phasing addition or a detection process on the processed element data, generating the reception data, and generating the ultrasound image, it is possible to generate an ultrasound image with high image quality, high brightness, and excellent sharpness.

Here, the generation of the processed element data is also referred to as a multiline process in the following description.

In the invention, the center element is the element in the center in the azimuth direction in a case where the number of openings of the transmission (the number of elements which perform the transmission of the ultrasonic waves) is an odd number.

On the other hand, in a case where the number of openings is an even number, any one of the elements in the center in the azimuth direction is set as the center element, or, assuming that there is an element in the middle of the azimuth direction, this element is set to be the center element. That is, in a case where the number of openings is an even number, the calculation may be performed by having a focus point on a line in the middle of the opening.

Here, as the superimposition processing method in the superimposition processor 49, an average value or a median value may be taken instead of only adding, or addition may be carried out after multiplication with a coefficient. Here, taking the average value or the median value may be considered equivalent to applying an averaging filter or a median filter at the element data level; however, an inverse filter or the like which performs a normal image process may also be applied instead of the averaging filter or the median filter.

Alternatively, when each of the element data to be superimposed is compared, the value is the maximum in a case where the element data are similar, the value is average in a case where the element data are not similar, and the value is intermediate in a case where the distribution is biased, but the superimposition process may be changed based on the feature amount of each of the element data to be superimposed without being limited thereto.

In addition, the number of element data to be superimposed on the element data of the element of interest is not limited to two in the example in the diagram and may be one or may be three or more. That is, the number of the element data to be superimposed on the element data of the element of interest may be appropriately set according to the required processing speed (the frame rate or the like), image quality, or the like.

Here, it is desirable that the number of element data to be superimposed on the element data of the element of interest match the extent of the spread of the beam width of the ultrasonic beam. Accordingly, in a case where the beam width changes according to the depth, the number of the element data to be superimposed may also be changed according to the depth.

In addition, since the beam width depends on the number of transmission openings, the number of element data to be superimposed may be changed according to the number of the transmission openings. Alternatively, the number of element data to be superimposed may be changed based on the feature amount such as the brightness value of the image or the like or the optimum number of element data to be superimposed may be selected from an image created by changing the number of element data to be superimposed into a plurality of patterns.

Here, in the multiline process above, the processed element data of the element data of the element of interest is generated by superimposing the element data where the center elements are different and which is obtained by a transmission of a plurality of ultrasonic beams for which the transmission direction of the ultrasonic beams is parallel (the angles are the same); however, the invention is not limited thereto.

For example, the processed element data may be generated by superimposing the element data where the center elements are the same and which is obtained by the transmission of a plurality of ultrasonic beams where the transmission directions (angles) are different. At this time, whether to generate the processed element data of the element data obtained by the transmission of any ultrasonic beam (that is, whether to generate the processed element data of the sound ray in any direction) may be set by default according to the examination site, the type of probe, or the like, or may be selected by the operator.

In addition, the processed element data may be generated using both of the element data where the center elements are different and which is obtained by the transmission of parallel ultrasonic beams and the element data where the center elements are the same and which is obtained by the transmission of ultrasonic beams with different transmission directions.

As described above, the element data processor 22 sends the generated processed element data to the image generator 24 (the phasing addition section 38). In addition, when determining (updating) the sound velocity of the subject, the element data processor 22 sends the generated processed element data to the sound velocity determiner 23 or the image generator 24.

In the image generator 24 to which the processed element data is supplied, as described above, the reception data is generated by performing a reception focusing process by the phasing addition section 38 carrying out phasing addition on the processed element data and the detection processor 40 generates B mode image data by carrying out attenuation correction and an envelope detection process on the reception data.

In addition, in the image generator 24, the DSC 48 raster converts the B mode image data into image data corresponding to a normal television signal scanning method and carries out a predetermined process such as a gradation process in the image processor 44.

The image processor 44 stores the generated B mode image data in the image memory 46 and/or sends the generated B mode image data to the display controller 26 to display a B mode image of the subject on the monitor 28.

On the other hand, the sound velocity determiner 23 determines the sound velocity (calculates the sound velocity) of the ultrasonic waves in the subject using the supplied processed element data.

Figure 8:
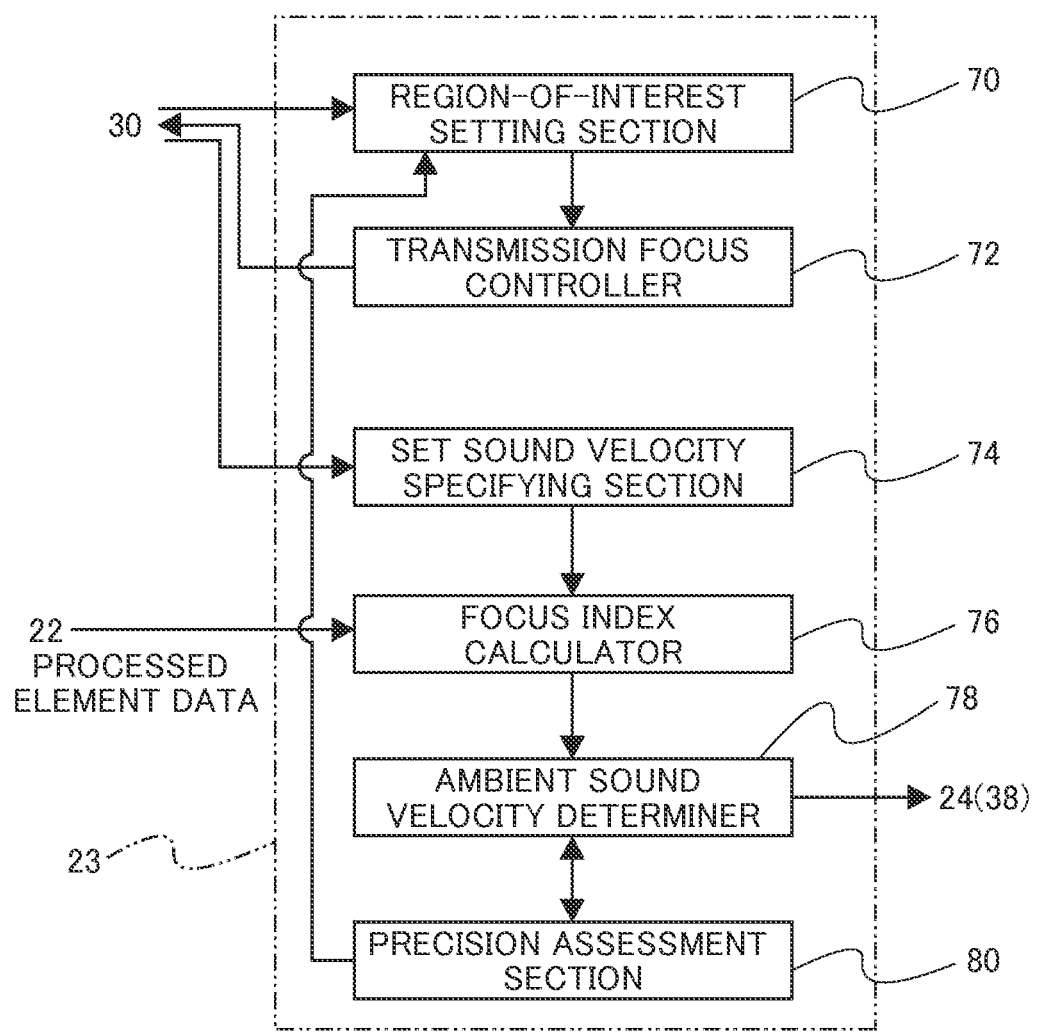
FIG. 8 is a block diagram conceptually illustrating an example of a configuration of a sound velocity determiner of the ultrasound diagnostic apparatus depicted in FIG. 1.

FIG. 8 is a block diagram conceptually illustrating the configuration of the sound velocity determiner 23.

As illustrated in FIG. 8, the sound velocity determiner 23 has a region-of-interest setting section 70, a transmission focus controller 72, a set sound velocity specifying section 74, a focus index calculator 76, an ambient sound velocity determiner 78, and a precision assessment section 80.

The region-of-interest setting section 70 sets the region-of-interest in the B mode image (in the ultrasound image) according to instructions from the controller 30.

In the sound velocity determiner 23, the sound velocity of the subject is determined for every region of interest.

In the present embodiment, the region-of-interest setting section 70 divides the entire screen of the B mode image into a grid pattern and set each of the resulting segments as a region of interest.

The number of divisions (the number in the grid) may be set in advance by default or it may be possible for the operator to optionally set the number in the azimuth direction and/or the depth direction. In a case where the number of divisions is set by default, there may be different settings for each image size or observation site. Furthermore, it may be possible for the operator to select from a plurality of divisions set in advance.

Here, in the invention, the region of interest is not limited to each region of the grid into which the B mode image is divided.

For example, all of the pixels (the positions (regions) corresponding to all of the pixels) generating the reception data (B mode image data) may be set as regions of interest. In other words, in an aspect where the screen is divided as described above, the screen may be divided into a grid corresponding to all of the pixels generating the reception data.

Alternatively, instead of the entire screen, a part of the screen which is set in advance or selected from a plurality of choices may be divided into a grid and parts thereof individually set as regions of interest. In addition, instead of the entire screen, the region of interest may be set in correspondence with an ROI set by the operator. Here, even in a case where the region of interest is set in a part of the screen or in the ROI, the division may be performed in the same manner as for the entire screen. In addition, it may be possible for the setting of the region of interest in the entire screen and the setting of the region of interest in the ROI to be selected by the operator.

In addition, the form of the division is not limited to a grid, for example, in the case of a B mode image with a fan shape such as an ultrasound image according to a convex probe, the form of the division may also be set to a fan shape according to this. In such a case, it is also possible to use each aspect described above.

Here, the region of interest may be changed or updated in a case where the image is greatly changed (in a case such as where the change value in the image feature amount exceeds a threshold), a case where the observation conditions are changed such as changes in the observation magnification or changes in the observation depth, or the like, and it may be possible for the operator to give an instruction for the changing or updating of the region of interest.

The region-of-interest setting section 70 also sets a focus point (the position of the focus point) in order to transmit (transmission focus) the ultrasonic waves corresponding to the determination of the sound velocity with respect to a set region of interest.

The focus point may be set by default in advance according to the observation site, the number of sound rays, the number of transmission and reception openings, the type of the probe 12, or the like, the operator may select or input instructions, or it may be possible to select between the default setting and operator instructions.

Here, as described above, with the invention which performs determination of the sound velocity using the processed element data where the superimposition of the element data is performed, it is possible to perform the transmission using multiple virtual focus points. Therefore, a plurality of positions of the focus points may be set with respect to one sound ray (the transmission and reception of ultrasonic waves in the same direction corresponding to one center element/one scanning line); however, one focus point is basically sufficient for one sound ray. Thus, according to the invention, it is possible to perform the determination of the sound velocity without reducing the frame rate.

In addition, the position of the focus points may be the same for all of the sound rays or sound rays with different focus points may be mixed in.

The region-of-interest setting section 70 sends the information on the set region of interest and the focus point (the position of the focus point) to the transmission focus controller 72.

The transmission focus controller 72 sends a transmission focus instruction to the controller 30 for the transmission section 14 to perform the transmission focus according to the region of interest and the focus point set by the region-of-interest setting section 70.

The set sound velocity specifying section 74 specifies a set sound velocity in order to perform reception focusing with respect to the reception data in the determination of the ambient sound velocity under the control of the controller 30.

The focus index calculator 76 calculates the focus index of the reception data by performing reception focusing with respect to the reception data for each of a plurality of set sound velocities specified by the set sound velocity specifying section 74 using the processed element data generated by the element data processor 22.

The ambient sound velocity determiner 78 determines the ambient sound velocity of the region of interest based on the focus index for each of a plurality of set sound velocities.

The precision assessment section 80 determines the precision of the sound velocity determined by the ambient sound velocity determiner 78.

In a case where the determined sound velocity has a predetermined precision or more, the precision determiner sends out an instruction to the ambient sound velocity determiner 78 to supply the determined sound velocity to the image generator 24 (phasing addition section 38). In contrast, in a case where the determined sound velocity does not satisfy a predetermined precision, an instruction is sent out to the region-of-interest setting section 70 to perform resetting of the focus points.

The precision assessment section 80 is provided as a preferable aspect of the invention.

Below, with reference to the flow chart illustrated in FIG. 9, detailed description will be given of the method of determining the sound velocity in the ultrasound diagnostic apparatus 10 (the sound velocity determining method of the invention).

The computer-readable recording medium of the invention is a recording medium recording the program which makes a computer execute the following sound velocity determining method in the ultrasound diagnostic apparatus 10.

In the ultrasound diagnostic apparatus 10, when determining the ambient sound velocity, first, the region-of-interest setting section 70 sets the region of interest and the focus point according to instructions from the controller 30 as described above.

Here, in the invention, the timing at which the ambient sound velocity is determined (the update timing of the ambient sound velocity) is not particularly limited and may be the same as for a known ultrasound diagnostic apparatus. For example, the determination of the ambient sound velocity may be performed only one time according to the measurement start instructions, the determination of the ambient sound velocity may be performed in a case where the image is greatly changed (in a case where a change value of a feature amount of the image exceeds a threshold, or the like), the determination of the ambient sound velocity may be performed every predetermined number of frames determined as appropriate or every time a predetermined time passes, the determination of the ambient sound velocity may be performed according to the input instructions of the operator, and it may be possible to appropriately select two or more timings for the sound velocity determination.

Regardless of the timing at which the ambient sound velocity is determined, since the transmission may basically be performed with one focus point with respect to one sound ray according to the invention which performs the multiline process, it is possible to avoid a decrease in the frame rate caused by the determination of the sound velocity, in contrast to the related art.

According to the setting of the region of interest, the transmission focus controller 72 sends a transmission focus instruction to the controller 30 so that the transmission section 14 executes the transmission focus to transmit the desired ultrasonic beam to the set region of interest and focus point.

Accordingly, the transmission section 14 transmits the ultrasonic beam to the subject by driving the probe 12 (the ultrasound transducers (elements) corresponding to the transducer array 36), the ultrasonic echoes reflected by the subject are received by the ultrasound transducers (elements), and an analog reception signal is output to the receiving section 16.

The receiving section 16 carries out a predetermined process such as amplification on the analog reception signal and supplies the result to the A/D converter 18.

The A/D converter 18 A/D converts the analog reception signal supplied from the receiving section 16 and sets the signal as element data which is a digital reception signal.

The element data is stored in the element data storage 20.

When the element data is stored in the element data storage, the element data processor 22 generates the processed element data by performing the multiline process described above.

That is, as illustrated in FIGS. 7A to 7H, with regard to, for example, the element of interest and both adjacent elements, the element data processor 22 calculates the delay time of the element data of both adjacent elements with respect to the element data of the element of interest, performs delay time correction and azimuth direction shifting on the element data of the adjacent element, and generates the processed element data of the element of interest by superimposing the element data of the adjacent elements on both sides on the element data of the element of interest.

The element data processor 22 supplies the generated processed element data to the sound velocity determiner 23 (the focus index calculator 76). Here, the element data processor 22 also supplies the generated processed element data for sound velocity determination to the image generator 24 and the image generator 24 may generate an ultrasound image (B mode image data) using the processed element data. In addition, the processed element data (the element data) generated for the sound velocity determination may be used only in the sound velocity determination.

The sound velocity determiner 23 determines the sound velocity of the ultrasonic waves in the subject using the supplied processed element data.

Figure 10:
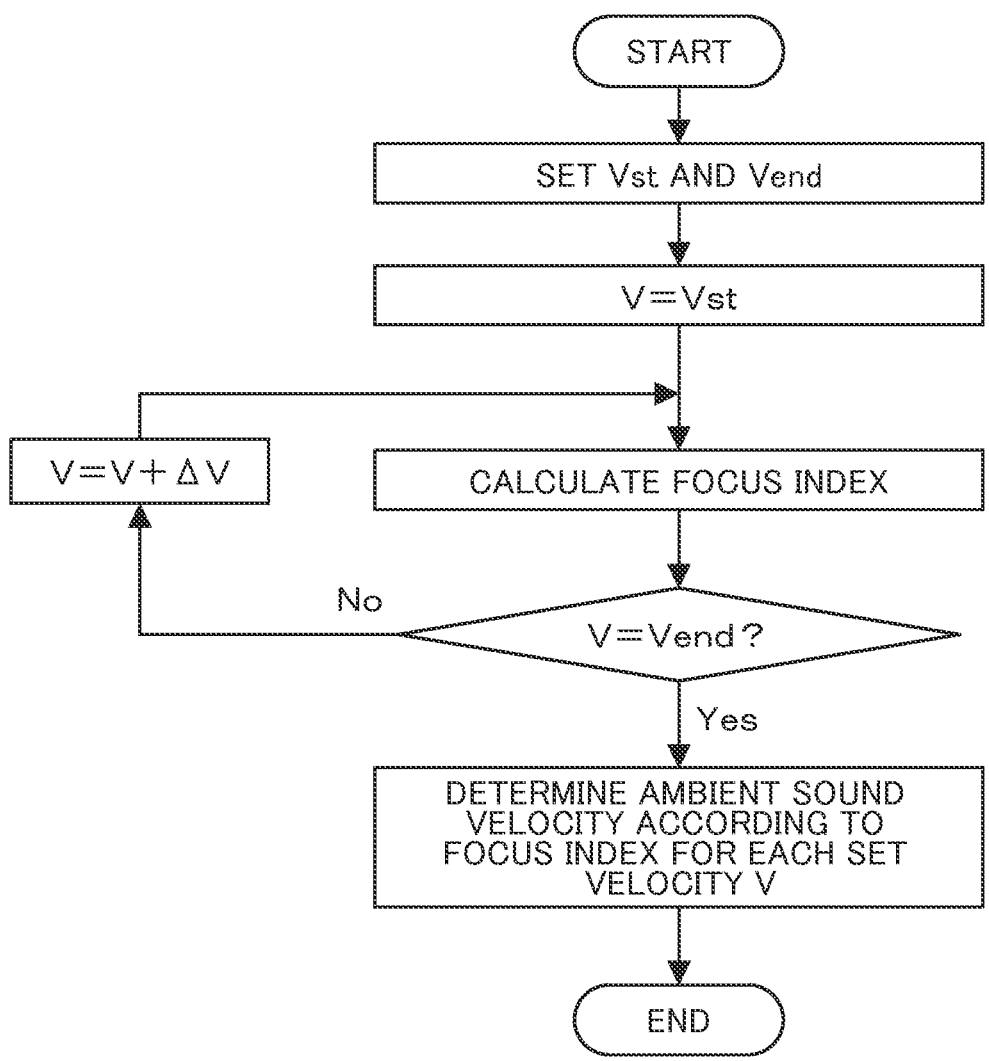
FIG. 10 is a flow chart for describing a sound velocity determining method in the flow chart of FIG. 9.

FIG. 10 illustrates a flow chart of an example of the sound velocity determining method in the sound velocity determiner 23. Here, in the invention, the sound velocity determining method in the sound velocity determiner 23 is not limited to this method and it is possible to use various sound velocity determining methods (methods of calculating the sound velocity) performed in the ultrasound diagnostic apparatus.

When the processed element data is supplied, the processed element data is stored in a predetermined site in the sound velocity determiner 23 if necessary. Also, first, the set sound velocity specifying section 74 sets the starting sound velocity Vst and the finishing sound velocity Vend of the set sound velocity V and further sets the starting sound velocity Vst of the set sound velocity V.

Set sound velocities including the start sound velocity Vst and the finishing sound velocity Vend may be set in advance as default values. Alternatively, only the start sound velocity Vst and the finishing sound velocity Vend may be input by the operator as desired, while only the step width therebetween (predetermined step sound velocity amount ΔV) may be set as a default value. Still alternatively, the operator may input the start sound velocity Vst, the finishing sound velocity Vend and the step width as desired. In addition, in a case where the set sound velocity or the step width is set by default, a plurality of types of set sound velocities are set according to the observation site, the gender of the subject, or the like, and can be selected as appropriate by the operator.

In the present example, as an example, 1410 m/sec is set as the starting sound velocity Vst and 1570 m/sec is set as the finishing sound velocity Vend and, accordingly, the set sound velocity is set at intervals of 40 m/sec as the predetermined step width.

Next, the focus index calculator 76 calculates the focus index of the reception data by carrying out reception focusing with respect to the processed element data for each of a plurality of set sound velocities specified by the set sound velocity specifying section 74 corresponding to each of the regions of interest.

Specifically, for the reception data (the ultrasound image data/ultrasound image) in the region of interest, the focus index calculator 76 calculates the integrated value, a squared integral value, a peak value, a degree of sharpness (sharpness), a contrast, a brightness value, a half-width, a frequency spectrum integration, a maximum value, a frequency spectrum integral value or squared integral value normalized by a DC component, an autocorrelation value, or the like as the focus index.

Next, the sound velocity determiner 23 determines whether or not the set sound velocity V reached the finishing sound velocity Vend in the set sound velocity specifying section 74, and, if the set sound velocity V is less than the finishing sound velocity Vend (No), the focus index of the region of interest is calculated by adding the predetermined step sound velocity amount ΔV, that is, 40 m/sec in the present example to the set sound velocity V.

This routine is repeated and when it is determined that the set sound velocity V has reached the finishing sound velocity Vend (Yes), the ambient sound velocity of the region of interest is determined by the ambient sound velocity determiner 78 based on the focus index for each of the plurality of set sound velocities by setting the set sound velocity with the highest focus index as the ambient sound velocity of the region of interest, or the like. For example, by setting the brightness of the ultrasound image as the focus index, the sound velocity obtained by the ultrasound image with the highest brightness in the region of interest is set as the ambient sound velocity of the region of interest.

That is, the ambient sound velocity in the present example is the average sound velocity of a region between the ultrasound probe 12 and the region of interest when the sound velocity from the probe 12 (the transducer array 36 (ultrasound transducers)) to a certain region of interest is assumed to be constant. As described above, the sound velocity determiner 23 performs the determination of the ambient sound velocity in this manner in all of the set regions of interest.

As described above, the processed element data generated in the multiline process is element data in such a case that the focus points are linked at a large number of points on the sound ray to be transmitted by eliminating the influence of the ghost, that is, element data obtained by the transmission of the ultrasonic waves at multiple virtual focus points.

Therefore, according to the invention which performs the determination of the sound rays using the processed element data, even with the transmission of ultrasonic waves at one focus point on one sound ray, it is possible to determine the sound velocity with high precision equal to or higher than in a case where the transmission of the ultrasound is performed at many focus points on one sound ray. In addition, since it is possible to determine the sound velocity with high precision in the transmission of ultrasonic waves at one focus point for one sound ray, it is also possible to prevent a decrease in the frame rate which accompanies the determination of the sound velocity (the updating of the sound velocity).

Here, when the ambient sound velocity of the region of interest is determined, the ambient sound velocity determiner 78 sends the determined ambient sound velocity to the precision assessment section 80.

As described above, even with the transmission of ultrasonic waves at one focus point, the processed element data obtained by the multiline process is element data for which ghosting is greatly attenuated and which is obtained by the transmission of ultrasonic waves at multiple virtual focus points. Therefore, determination of the sound velocity with high precision is possible at the same level as for the sound velocity determined by transmission of ultrasonic waves at multiple focus points.

However, even using the processed element data, the possibility of determining an improper sound velocity is not zero (for example, in the vicinity of the focus point of the transmission to be described below or the like).

With respect to this, as a preferable aspect, the precision assessment section 80 is provided in the ultrasound diagnostic apparatus 10 in the example in the diagram and assesses the precision of the determined ambient sound velocity.

As a result, in a case where the precision of the ambient sound velocity is a predetermined precision or more (hereinafter, also referred to as "satisfactory" or "satisfactory sound velocity"), the precision assessment section 80 sends out an instruction to the ambient sound velocity determiner 78 to send the ambient sound velocity of the region of interest to the image generator 24 (end).

In contrast, in a case where the precision of the ambient sound velocity is less than a predetermined precision (hereinafter, also referred to as "unsatisfactory" or "unsatisfactory sound velocity"), the precision assessment section 80 sends out an instruction to the region-of-interest setting section 70 to set a focus point which is different to the previous focus point for the region of interest with the unsatisfactory sound velocity, redetermines the ambient sound velocity by returning to the step of "setting the region of interest and focus point", changing the focus point and performing transmission and reception of the ultrasonic waves again, and assesses the precision of the ambient sound velocity.

In the ultrasound diagnostic apparatus 10, the redetermination of the ambient sound velocity is repeatedly performed until the sound velocity is satisfactory in the corresponding region of interest and the sound velocity is set to be satisfactory in all the regions of interest.

Due to this, by using the multiline process, it is possible to determine the sound velocity with equal or higher precision while avoiding a decrease in the frame rate to be lower than in the sound velocity determination of the related art.

The precision assessment method of the ambient sound velocity is not particularly limited and it is possible to use various known assessment methods.

As an example, there is a method where, after dividing an image into predetermined regions formed of a plurality of regions of interest (for example, a square grid shape if the probe is a linear type, a fan shaped grid shape if the probe is a convex type, or the like) and calculating the standard deviation of the ambient sound velocity in the predetermined regions, the region of interest of the predetermined region is assessed as unsatisfactory sound velocity in a case where the standard deviation does not satisfy a threshold set in advance.

In addition, it is also possible to use a method where in a similar predetermined region, in a case where the maximum value and the minimum value of the ambient sound velocity are detected and the difference therebetween exceeds a predetermined threshold, the sound velocity is assessed to be unsatisfactory for the region of interest of the predetermined region. In addition, it is also possible to use a method where, in a similar predetermined region, in a case where the average value of the ambient sound velocity is calculated and the average value is outside a predetermined range, the sound velocity is assessed to be unsatisfactory for the region of interest of the predetermined region. In addition, it is also possible to use a method where, in a similar predetermined region, in a case where the frequency distribution of the ambient sound velocity is calculated and the variation in the distribution exceeds a predetermined threshold, the sound velocity is assessed to be unsatisfactory for the region of interest of the predetermined region.

Alternatively, it is also possible to use a method where, in a similar predetermined region, the average value of the ambient sound velocity is calculated and, for a region of interest where the difference between the average values exceeds a predetermined threshold, the sound velocity is assessed to be unsatisfactory.

Furthermore, for the ambient sound velocity of the predetermined region, satisfactory sound velocity and unsatisfactory sound velocity may be decided using an integrated value, a squared integral value, a peak value, a contrast, a frequency spectrum integration, a frequency spectrum integral value or a squared integral value normalized by a maximum value or a DC component, an autocorrelation value, or the like.

Here, when assessing the precision of the ambient sound velocity in this manner, the determination (redetermination) of the ambient sound velocity of each region of interest may of course be performed at the same time.

As long as the transmission of ultrasonic waves where the focus points are changed corresponding to the region of interest for which the redetermination is performed is performed, the redetermination of the ambient sound velocity may be performed using the same method as the previous sound velocity determination, or using a different method.

The ambient sound velocity may be re-determined using the processed element data obtained by performing the same multiline process after performing the transmission of the ultrasonic waves with the focus point changed corresponding to the region of interest where the ambient sound velocity has not reached a predetermined precision. Alternatively, the sound velocity may be determined using the normal element data on which the multiline process is not performed by performing transmission of the ultrasonic waves where the focus points are matched in the region of interest where the redetermination of the ambient sound velocity is performed. In addition, the method for calculating the ambient sound velocity determination may be changed, for instance, changing the focus guide. Alternatively, the redetermination of the ambient sound velocity may be performed by selecting from these methods.

As described above, since it is possible to perform the transmission of the ultrasonic waves as with the multiple virtual focus points when the multiline process is performed, it is possible to perform the determination of the ambient sound velocity with high precision at the same level or higher as the transmission with multiple focus points, even with the transmission of ultrasonic waves at one focus point with respect to one sound ray.

Here, as can be understood from the calculation method of the delay time described above, the processing of the element data in the multiline process is performed regarding the focus points as ideal point sound sources. Therefore, in cases where the focus points cannot be regarded as the ideal point sound sources, there are also cases where it is not possible to determine the ambient sound velocity with sufficient precision in the vicinity of the focus points.

According to this, in the ultrasound diagnostic apparatus 10, as illustrated in the flow chart in FIG. 11, in a case where the precision of the ambient sound velocity is assessed and the ambient sound velocity of the region of interest is less than a predetermined precision (unsatisfactory sound velocity), whether or not the region of interest is in the vicinity of the focus point (including the focus point) is determined, and the processing method of the redetermination of the ambient sound velocity may be changed thereafter according to the determination result.

Figure 9:
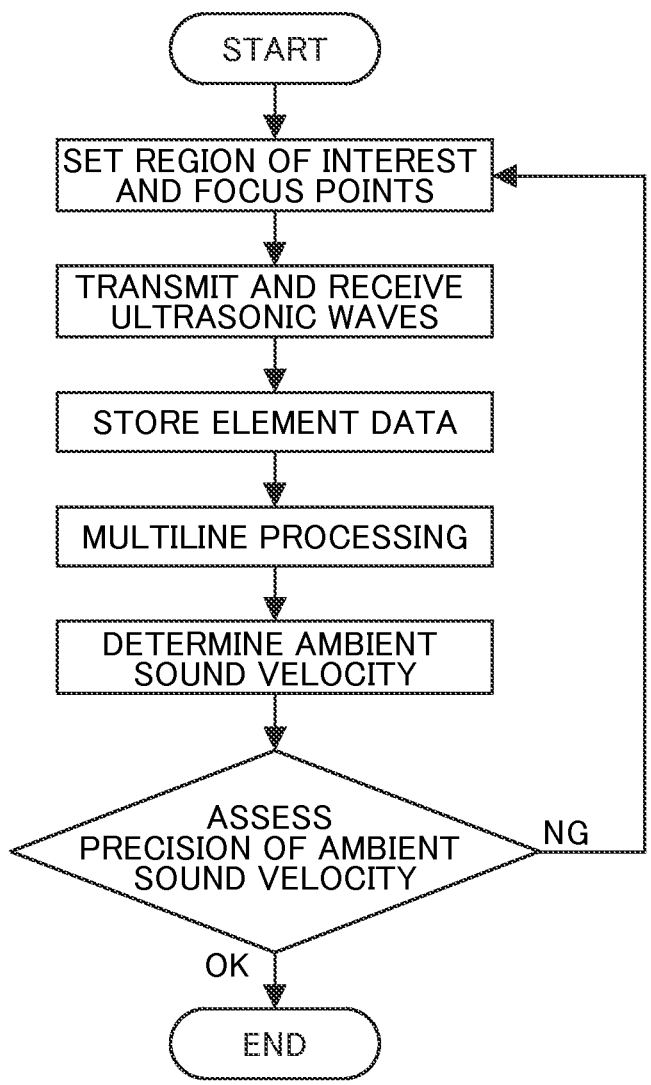
FIG. 9 is a flow chart for describing an example of a sound velocity determining process of the ultrasound diagnostic apparatus depicted in FIG. 1.

In the determination of the ambient sound velocity illustrated in the flow chart in FIG. 11, the process is performed in the same manner as the determination of the ambient sound velocity illustrated in FIG. 9 described above from the start of the sound velocity determination up to the precision assessment of the ambient sound velocity.

In a case where the result of the precision assessment of the ambient sound velocity is satisfactory sound velocity, as before, the precision assessment section 80 sends out an instruction to the ambient sound velocity determiner 78 to send the ambient sound velocity of the region of interest to the image generator 24 (end).

In contrast, in a case where the result is unsatisfactory sound velocity, the precision assessment section 80 determines whether or not the region of interest is in the vicinity of the focus point of the ultrasonic beam transmission.

Here, in the invention, as an example, the vicinity of the focus point is a position within 10 mm from the position of the focus point.

As a result, in a case where the region of interest with unsatisfactory sound velocity is not in the vicinity of the focus point (No), as before, an instruction is sent out to the region-of-interest setting section 70 to set a different focus point for the region of interest, the ambient sound velocity is redetermined by returning to the step of "setting the region of interest and focus point", changing the focus point and performing transmission and reception of the ultrasonic waves again, and the precision is assessed.

In contrast, in a case where the region of interest with unsatisfactory sound velocity is in the vicinity of the focus point, an instruction is sent out to the ambient sound velocity determiner 78 to read out the element data corresponding to the region of interest from the element data storage 20 and determine the ambient sound velocity using the element data.

As described above, in a case where the ambient sound velocity is determined using normal element data instead of processed element data, it is possible to accurately determine the ambient sound velocity in a region where the wavefront shape of the reflected waves such as the focus point is clear. Accordingly, in a case where the sound velocity is unsatisfactory, it is determined whether or not the region of interest is in the vicinity of the focus point. Then, in a case where the region of interest is in the vicinity of the focus point, by redetermining the ambient sound velocity using the element data, it is possible to redetermine the ambient sound velocity with high precision without performing transmission and reception of ultrasonic waves again.

Here, the determining of the ambient sound velocity using the element data may be performed using a known method in the same manner as the determining of the ambient sound velocity using the processed element data. In addition, the determining of the ambient sound velocity using the element data may be performed in the same manner as the processed element data, or the ambient sound velocity may be determined (calculated) using a different method.

In the example illustrated in FIG. 11, the redetermining of the sound velocity and the precision assessment are repeatedly performed until the sound velocity is satisfactory in all of the regions of interest.

In addition, in a case where the redetermined sound velocity in the vicinity of the focus point is unsatisfactory, the redetermining of the sound velocity may be performed using the element data by resetting the focus points inside the region of interest with the unsatisfactory sound velocity and performing the transmission and reception of the ultrasonic waves. Alternatively, the redetermining of the sound velocity may be performed using the processed element data on which the multiline process is performed by resetting the position of the focus point to a position separated from the region of interest. Alternatively, it may be possible to select either of the above.

Alternatively, the ambient sound velocity of the region of interest with the unsatisfactory sound velocity may be calculated by interpolation using the ambient sound velocity where the sound velocity is satisfactory in the periphery, or the ambient sound velocity where the sound velocity is satisfactory in the periphery may be used as is as the ambient sound velocity of the region of interest with the unsatisfactory sound velocity.

The ultrasound diagnostic apparatus, the sound velocity determining method, and the program of the invention have been described above; however, the invention is not limited to the examples described above and various improvements or modifications may be made within a range which does not depart from the gist of the invention as a matter of course.

For example, in the ultrasound diagnostic apparatus 10 of the example in the diagram, the image generator 24 generates an ultrasound image using processed element data generated by a multiline process as a preferable embodiment; however, the invention is not limited thereto.

That is, when the ultrasound diagnostic apparatus of the invention performs the sound velocity determination of the ultrasonic waves in the subject using the processed element data generated using the multiline process, the generation of the ultrasound image may be performed using the normal element data.

In addition, in order to perform the multiline process to be described below without having the element data storage 20 which stores the element data for one image, the transmission and reception of the ultrasonic waves may be performed every time or a necessary number of times corresponding to one element-of-interest.

In addition, in the ultrasound diagnostic apparatus 10 in the example in the diagram, the region-of-interest setting section 70 is configured to divide the entire screen or a part thereof into a lattice shape, set individual parts thereof as regions of interest, and individually determine the optimum sound velocity for each region; however, the invention is not limited thereto and the entire screen may be set as one region of interest. That is, as in the related art, as a configuration where one optimum sound velocity is determined for the entire screen, a configuration may be adopted which uses processed element data when determining the optimum sound velocity for the entire screen.

What is claimed is:

1. An ultrasound diagnostic apparatus, which inspects an inspection object using an ultrasonic beam, comprising:
    a probe in which a plurality of elements are arranged, which transmit the ultrasonic beam, receive ultrasonic echoes reflected by the inspection object, and output an analog element signal according to the received ultrasonic echoes;
    a transmitter configured to make the probe perform transmission of the ultrasonic beam so as to each form a predetermined transmission focus point using the plurality of elements;
    a receiver configured to receive an analog element signal output by the plurality of elements corresponding to the individual transmission of the ultrasonic beam, and carry out a predetermined process;
    an analog-to-digital converter configured to analog-to-digital convert the analog element signal processed by the receiver into first element data which is a digital element signal, the first element data indicating a relationship between an element position, depth and signal strength;
    a data processor configured to generate second element data corresponding to the first element data of an element of interest which is any one of center elements at the time of transmission and reception of the ultrasonic waves among a plurality of first element data, the second element data indicating a relationship between an element position, depth and signal strength;
    a sound velocity determiner configured to determine a sound velocity in the inspection object using the second element data;
    and an image generator configured to generate a sound ray signal by performing phasing addition using the second element data or the first element data and information on the sound velocity, and generate an ultrasound image from a plurality of sound ray signals,
    wherein the data processor comprises a delay time calculator and a superimposition processor;
    the transmitter, the receiver, the analog-to-digital converter, the data processor, the sound velocity determiner, the delay time calculator, and the superimposition processor are configured by a CPU and an operation program or a digital circuit;
    one of the first element data is obtained by performing the transmission of the ultrasonic beam with the transmitter once and analog-to-digital converting a plurality of analog element signals output by a plurality of elements that receive ultrasonic echoes;
    the element position indicated by the first element data is a position of an element corresponding to each of the plurality of analog element signals, the depth indicated by the first element data is calculated based on a time from the transmission of the ultrasonic beam to reception of the ultrasonic beam, and the signal strength indicated by the first element data is calculated based on a signal strength of the analog element signal;
    the transmitter and the receiver transmit and receive ultrasonic waves a plurality of times and the analog-to-digital converter generates a plurality of first element data corresponding to a plurality of transmissions and receptions;
    the first element data and the second element data are data before phasing addition;
    the data processor generates a plurality of second element data by changing the element of interest a plurality of times;
    the delay time calculator is configured to calculate a delay time for each other first element data with respect to the first element data of the element of interest based on at least one piece of information concerning the probe, the sound velocity in the inspection object, a position of a focus point of the ultrasonic beam, a transmission opening in the probe, and a reception opening in the probe; and
    the superimposition processor acquires the first element data of the element of interest and at least one of first element data in which a central element at the time of ultrasonic beam transmission is different from that of the first element data of the element of interest to be superimposed based on information relating to a number of element data to be superimposed and a superimposition process method, and shifts the first element data different in central element by an amount of deviation with respect to the central element of the first element data of the element of interest, and performs delay time correction on the first element data different in central element, and performs addition or averaging of the first element data of the element of interest and the first element data different in central element to generate second element data.

2. The ultrasound diagnostic apparatus according to claim 1, wherein the transmitter makes the probe perform transmission of the ultrasonic beam a plurality of times, changing at least one of a center element and a transmission direction of the ultrasonic beam.

3. The ultrasound diagnostic apparatus according to claim 2, wherein the data processor generates the second element data using at least one of a plurality of the first element data obtained by transmission of the ultrasonic beam where the center element is different to each other and a plurality of the first element data obtained by transmission of the ultrasonic beam where the transmission direction is different to each other.

4. The ultrasound diagnostic apparatus according to claim 1, wherein the data processor generates the second element data from a plurality of the first element data obtained by transmission of the ultrasonic beam where transmission regions overlap.

5. The ultrasound diagnostic apparatus according to claim 1, further comprising an assessment section configured to assess precision of the determined sound velocity.

6. The ultrasound diagnostic apparatus according to claim 5, wherein the sound velocity is determined in a plurality of positions inside the inspection object and the precision of the sound velocity is assessed at each position.

7. The ultrasound diagnostic apparatus according to claim 6, wherein the assessment of the precision of the sound velocity is performed using at least one of variation in the sound velocity, standard deviation in the sound velocity, a difference between a maximum value and a minimum value of the sound velocity, and an average value of the sound velocity.

8. The ultrasound diagnostic apparatus according to claim 1, further comprising an element data storage configured to store all of the first element data corresponding to at least one ultrasound image.

9. The ultrasound diagnostic apparatus according to claim 1, wherein an ultrasound image is formed using the second element data.

10. The ultrasound diagnostic apparatus according to claim 1, wherein an ultrasound image is formed by performing phasing addition for forming the ultrasound image using the sound velocity determined by the sound velocity determiner.

11. A sound velocity determining method for ultrasound diagnosis using a probe in which a plurality of elements are arranged, which transmit an ultrasonic beam, receive ultrasonic echoes reflected by an inspection object, and output an analog element signal according to the received ultrasonic echoes, the method comprising the steps of:
   making the probe perform transmission of the ultrasonic beam so as to each form a predetermined transmission focus point using the plurality of elements when determining a sound velocity inside the inspection object and outputting analog element signals from the plurality of elements corresponding to the individual transmission of ultrasonic beams;
   analog-to-digital converting the analog element signal into first element data which is a digital element signal, the first element data indicating a relationship of an element position, depth and signal strength;
   wherein one of the first element data is obtained by performing the transmission of the ultrasonic beam with the transmitter once and analog-to-digital converting a plurality of analog element signals output by a plurality of elements that receive ultrasonic echoes; and
   wherein information on the element position indicated by the first element data refers to a position of an element corresponding to each of the plurality of analog element signals, information on the depth indicated by the first element data is calculated based on a time from the transmission of the ultrasonic beam to reception of the ultrasonic beam, and information on the signal strength indicated by the first element data is calculated based on a signal strength of the analog element signal;
   transmitting and receiving ultrasonic waves a plurality of times and generating a plurality of first element data corresponding to a plurality of transmissions and receptions;
   generating second element data corresponding to the first element data of an element of interest which is any one of center elements at the time of transmission and reception of the ultrasonic waves among a plurality of the first element data, the second element data indicating a relationship between an element position, depth and signal strength;
   generating a plurality of second element data by changing the element of interest a plurality of times;
   determining the sound velocity inside the inspection object using the second element data; and
   generating a sound ray signal by performing phasing addition using a plurality of second element data or a plurality of first element data and information on the sound velocity, and generating an ultrasound image from a plurality of sound ray signals,
   wherein the first element data and the second element data are data before phasing addition;
   the step of generating the second element data including:
   calculating a delay time for each other first element data with respect to the first element data of the element of interest based on at least one piece of information concerning the probe, the sound velocity in the inspection object, a position of a focus point of the ultrasonic beam, a transmission opening in the probe, and a reception opening in the probe; and
   acquiring the first element data of the element of interest and at least one of first element data in which a central element at the time of ultrasonic beam transmission is different from that of the first element data of the element of interest to be superimposed based on information relating to a number of element data to be superimposed and a superimposition process method, and shifts the first element data different in central element by an amount of deviation with respect to the central element of the first element data of the element of interest, and performs delay time correction on the first element data different in central element, and performing addition or averaging of the first element data of the element of interest and the first element data different in central element to generate second element data.

12. The sound velocity determining method according to claim 11, wherein the probe is made perform transmission of the ultrasonic beam a plurality of times, changing at least one of a center element and a transmission direction of the ultrasonic beam.

13. The sound velocity determining method according to claim 12, wherein the second element data is generated using at least one of a plurality of the first element data obtained by transmission of the ultrasonic beam where the center element is different to each other and a plurality of the first element data obtained by transmission of the ultrasonic beams where the transmission direction is different to each other.

14. The sound velocity determining method according to claim 11, wherein the second element data is generated from a plurality of the first element data obtained by transmission of the ultrasonic beam where transmission regions overlap.

15. The sound velocity determining method according to claim 11, further comprising assessing precision of the determined sound velocity.

16. The sound velocity determining method according to claim 15, wherein the sound velocity is determined at a plurality of positions inside the inspection object and the precision of the sound velocity is assessed for each position.

17. The sound velocity determining method according to claim 16, wherein the assessment of the precision of the sound velocity is performed using at least one of variation in the sound velocity, standard deviation in the sound velocity, a difference between a maximum value and a minimum value of the sound velocity, and an average value of the sound velocity.

18. A non-transitory computer-readable medium that records a program making a computer execute the steps of:
   making a probe, in which a plurality of elements are arranged and which transmit an ultrasonic beam, receive ultrasonic echoes reflected by an inspection object, and output an analog element signal according to the received ultrasonic echoes, perform transmission of the ultrasonic beam so as to each form a predetermined transmission focus point using the plurality of elements and outputting of an analog element signal from the plurality of elements corresponding to the individual transmission of the ultrasonic beam;
   analog-to-digital converting the analog element signal into first element data which is a digital element signal, the first element data indicating a relationship between an element position, depth and signal strength;
   generating second element data corresponding to the first element data of an element of interest which is any one of central elements at the time of transmission and reception of the ultrasonic waves among a plurality of the first element data, the second element data indicating a relationship between an element position, depth and signal strength;

determining the sound velocity inside the inspection object using the second element data; and generating a sound ray signal by performing phasing addition using a plurality of second element data or a plurality of first element data and information on the sound velocity, and generating an ultrasound image from a plurality of sound ray signals, wherein one of the first element data is obtained by performing the transmission of the ultrasonic beam with the transmitter once and analog-to-digital converting a plurality of analog element signals output by a plurality of elements that receive ultrasonic echoes; and wherein information on the element position indicated by the first element data refers to a position of an element corresponding to each of the plurality of analog element signals, information on the depth indicated by the first element data is calculated based on a time from the transmission of the ultrasonic beam to reception of the ultrasonic beam, and information on the signal strength indicated by the first element data is calculated based on a signal strength of the analog element signal;

transmitting and receiving ultrasonic waves a plurality of times and generating a plurality of first element data corresponding to a plurality of transmissions and receptions;

generating a plurality of second element data by changing the element of interest a plurality of times;

wherein the first element data and the second element data are data before phasing addition;

the step of generating the second element data including:

calculating a delay time for each other first element data with respect to the first element data of the element of interest based on at least one piece of information concerning the probe, the sound velocity in the inspection object, a position of a focus point of the ultrasonic beam, a transmission opening in the probe, and a reception opening in the probe; and acquiring the first element data of the element of interest and at least one of first element data in which a central element at the time of ultrasonic beam transmission is different from that of the first element data of the element of interest to be superimposed based on information relating to a number of element data to be superimposed and a superimposition process method, and shifts the first element data different in central element by an amount of deviation with respect to the central element of the first element data of the element of interest, and performs delay time correction on the first element data different in central element, and performing addition or averaging of the first element data of the element of interest and the first element data different in central element to generate second element data.

19. The non-transitory computer-readable medium that records the program according to claim 18, wherein, in the outputting of the analog element signal from the plurality of elements, the probe is made perform transmission of the ultrasonic beam a plurality of times, changing at least one of a center element and a transmission direction of the ultrasonic beam.

20. The non-transitory computer-readable medium that records the program according to claim 19, wherein, in the generating of the second element data, the second element data is generated using at least one of a plurality of the first element data obtained by transmission of the ultrasonic beam where the center element is different to each other and a plurality of the first element data obtained by transmission of the ultrasonic beam where the transmission direction is different to each other.

21. The non-transitory computer-readable medium that records the program according to claim 18, wherein, in the generating of the second element data, the second element data is generated from a plurality of the first element data obtained by transmission of the ultrasonic beam where transmission regions overlap.

* * * * *